US011817179B2

(12) United States Patent
Chudova et al.

(10) Patent No.: US 11,817,179 B2
(45) Date of Patent: Nov. 14, 2023

(54) METHODS FOR MULTI-RESOLUTION ANALYSIS OF CELL-FREE NUCLEIC ACIDS

(71) Applicant: GUARDANT HEALTH, INC., Palo Alto, CA (US)

(72) Inventors: Darya Chudova, San Jose, CA (US); Helmy Eltoukhy, Atherton, CA (US); Stefanie Ann Ward Mortimer, Morgan Hill, CA (US); Diana Abdueva, Orinda, CA (US)

(73) Assignee: Guardant Health, Inc., Palo Alto, CA (US)

( * ) Notice: Subject to any disclaimer, the term of this patent is extended or adjusted under 35 U.S.C. 154(b) by 0 days.

(21) Appl. No.: 18/155,523

(22) Filed: Jan. 17, 2023

(65) Prior Publication Data

US 2023/0260596 A1 Aug. 17, 2023

Related U.S. Application Data

(63) Continuation of application No. 18/055,298, filed on Nov. 14, 2022, which is a continuation of application
(Continued)

(51) Int. Cl.
*G16B 30/00* (2019.01)
*C12Q 1/6806* (2018.01)
(Continued)

(52) U.S. Cl.
CPC .......... *G16B 30/00* (2019.02); *C12Q 1/6806* (2013.01); *C12Q 1/6827* (2013.01); *G16B 5/00* (2019.02);
(Continued)

(58) Field of Classification Search
CPC .......... G16B 30/00; G16B 5/00; G16B 40/30; C12Q 1/6806; C12Q 2535/122; C12Q 2537/159

See application file for complete search history.

(56) References Cited

U.S. PATENT DOCUMENTS

| 5,648,245 A | 7/1997 | Fire et al. |
| 5,952,170 A | 9/1999 | Stroun et al. |

(Continued)

FOREIGN PATENT DOCUMENTS

| EP | 1647600 A2 | 6/2006 |
| EP | 1712639 B1 | 8/2008 |

(Continued)

OTHER PUBLICATIONS

Buermans, H. P. J., and J. T. Den Dunnen. "Next generation sequencing technology: advances and applications." Biochimica et Biophysica Acta (BBA)—Molecular Basis of Disease 1842.10 (2014): 1932-1941. (Year: 2014).*

(Continued)

*Primary Examiner* — Larry D Riggs, II
*Assistant Examiner* — Guozhen Liu
(74) *Attorney, Agent, or Firm* — Timothy A. Hott

(57) ABSTRACT

The present disclosure provides a method for enriching for multiple genomic regions using a first bait set that selectively hybridizes to a first set of genomic regions of a nucleic acid sample and a second bait set that selectively hybridizes to a second set of genomic regions of the nucleic acid sample. These bait set panels can selectively enrich for one or more nucleosome-associated regions of a genome, said nucleosome-associated regions comprising genomic regions having one or more genomic base positions with differential nucleosomal occupancy, wherein the differential nucleosomal occupancy is characteristic of a cell or tissue type of origin or disease state.

19 Claims, 6 Drawing Sheets

Specification includes a Sequence Listing.

Related U.S. Application Data

No. 17/383,385, filed on Jul. 22, 2021, which is a continuation of application No. 16/338,445, filed as application No. PCT/US2017/054607 on Sep. 29, 2017, now abandoned.

(60) Provisional application No. 62/489,391, filed on Apr. 24, 2017, provisional application No. 62/468,201, filed on Mar. 7, 2017, provisional application No. 62/402,940, filed on Sep. 30, 2016.

(51) Int. Cl.
    *G16B 40/30*     (2019.01)
    *G16B 20/20*     (2019.01)
    *C12Q 1/6827*     (2018.01)
    *G16B 5/00*     (2019.01)
    *G16B 25/10*     (2019.01)

(52) U.S. Cl.
CPC ............. *G16B 25/10* (2019.02); *G16B 40/30* (2019.02); *C12Q 2535/122* (2013.01); *C12Q 2537/159* (2013.01)

(56) References Cited

U.S. PATENT DOCUMENTS

| | | |
|---|---|---|
| 6,492,121 B2 | 12/2002 | Kurane et al. |
| 6,586,177 B1 | 7/2003 | Shuber |
| 6,849,403 B1 | 2/2005 | Shuber |
| 6,858,412 B2 | 2/2005 | Willis et al. |
| 6,964,846 B1 | 11/2005 | Shuber |
| 7,163,789 B2 | 1/2007 | Chen et al. |
| 7,410,764 B2 | 8/2008 | Gocke et al. |
| 7,424,371 B2 | 9/2008 | Kamentsky |
| 7,537,897 B2 | 5/2009 | Brenner et al. |
| 7,700,286 B2 | 4/2010 | Stroun et al. |
| 7,727,720 B2 | 6/2010 | Dhallan |
| 7,803,929 B2 | 9/2010 | Melkonyan et al. |
| 7,811,757 B2 | 10/2010 | Shuber |
| 7,824,889 B2 | 11/2010 | Vogelstein et al. |
| 7,838,647 B2 | 11/2010 | Hahn et al. |
| 7,915,015 B2 | 3/2011 | Vogelstein et al. |
| 7,935,487 B2 | 5/2011 | Gocke et al. |
| 7,937,225 B2 | 5/2011 | Mishra et al. |
| 7,972,817 B2 | 7/2011 | Kopreski |
| 7,981,612 B2 | 7/2011 | Shuber et al. |
| 8,338,838 B2 | 12/2012 | Sun et al. |
| 8,383,338 B2 | 2/2013 | Kitzman et al. |
| RE44,596 E | 11/2013 | Stroun et al. |
| 8,603,749 B2 | 12/2013 | Gillevet |
| 8,614,073 B2 | 12/2013 | Eijk et al. |
| 8,685,678 B2 | 4/2014 | Casbon et al. |
| 8,741,606 B2 | 6/2014 | Casbon et al. |
| 9,018,365 B2 | 4/2015 | Brenner |
| 9,260,753 B2 | 2/2016 | Xie et al. |
| 9,340,830 B2 | 5/2016 | Lipson et al. |
| 9,376,719 B2 | 6/2016 | Eijk et al. |
| 9,404,156 B2 | 8/2016 | Hicks et al. |
| 9,574,230 B2 | 2/2017 | Eijk et al. |
| 9,657,335 B2 | 5/2017 | Eijk et al. |
| 9,670,542 B2 | 6/2017 | Eijk et al. |
| 9,745,627 B2 | 8/2017 | Eijk et al. |
| 9,850,523 B1 | 12/2017 | Chudova et al. |
| 11,062,791 B2 | 7/2021 | Chudova et al. |
| 2002/0072058 A1 | 6/2002 | Voelker et al. |
| 2005/0221314 A1 | 10/2005 | Berlin et al. |
| 2006/0073506 A1 | 4/2006 | Christians et al. |
| 2007/0065823 A1 | 3/2007 | Dressman et al. |
| 2008/0014146 A1 | 1/2008 | Hoff et al. |
| 2008/0124721 A1 | 5/2008 | Fuchs et al. |
| 2008/0131887 A1 | 6/2008 | Stephan et al. |
| 2008/0161420 A1 | 7/2008 | Shuber |
| 2009/0029377 A1 | 1/2009 | Lo et al. |
| 2009/0098547 A1 | 4/2009 | Ghosh |
| 2009/0105959 A1 | 4/2009 | Braverman et al. |
| 2009/0162836 A1 | 6/2009 | Widschwendter |
| 2009/0318305 A1 | 12/2009 | Lin et al. |
| 2010/0029498 A1 | 2/2010 | Gnirke et al. |
| 2010/0069250 A1 | 3/2010 | White et al. |
| 2010/0143932 A1 | 6/2010 | Lapidus |
| 2010/0196898 A1 | 8/2010 | Sugarbaker et al. |
| 2010/0323348 A1 | 12/2010 | Hamady et al. |
| 2011/0171640 A1 | 7/2011 | Bhatt et al. |
| 2011/0201507 A1 | 8/2011 | Rava et al. |
| 2011/0245482 A1 | 10/2011 | Hahn et al. |
| 2012/0046877 A1 | 2/2012 | Hyland et al. |
| 2012/0095697 A1 | 4/2012 | Halpern et al. |
| 2012/0208706 A1 | 8/2012 | Downing et al. |
| 2012/0316074 A1 | 12/2012 | Saxonov |
| 2013/0005585 A1 | 1/2013 | Anderson et al. |
| 2013/0022977 A1 | 1/2013 | Lapidus et al. |
| 2013/0137588 A1 | 5/2013 | Shendure et al. |
| 2013/0178373 A1 | 7/2013 | Rabinowitz et al. |
| 2013/0210643 A1 | 8/2013 | Casbon et al. |
| 2013/0224743 A1 | 8/2013 | Casbon et al. |
| 2013/0237458 A1 | 9/2013 | Casbon et al. |
| 2013/0267424 A1 | 10/2013 | Casbon et al. |
| 2014/0066317 A1 | 3/2014 | Talasaz |
| 2014/0287408 A1 | 9/2014 | Su et al. |
| 2014/0303008 A1 | 10/2014 | Schutz et al. |
| 2015/0126377 A1 | 5/2015 | Gnirke et al. |
| 2015/0299812 A1 | 10/2015 | Talasaz |
| 2015/0368708 A1 | 12/2015 | Talasaz |
| 2016/0032396 A1 | 2/2016 | Diehn et al. |
| 2016/0040229 A1 | 2/2016 | Talasaz et al. |
| 2016/0046986 A1 | 2/2016 | Eltoukhy et al. |
| 2016/0053301 A1 | 2/2016 | Raymond et al. |
| 2016/0060691 A1 | 3/2016 | Giresi et al. |
| 2016/0251704 A1 | 9/2016 | Talasaz et al. |
| 2016/0281166 A1 | 9/2016 | Bhattacharjee et al. |
| 2016/0333417 A1 | 11/2016 | Talasaz |
| 2016/0376647 A1 | 12/2016 | Travers et al. |
| 2017/0024513 A1 | 1/2017 | Lo et al. |
| 2017/0051347 A1 | 2/2017 | Vogelstein et al. |
| 2017/0058332 A1 | 3/2017 | Kermani et al. |
| 2017/0061072 A1 | 3/2017 | Kermani et al. |
| 2017/0073774 A1 | 3/2017 | Lo et al. |
| 2017/0107576 A1 | 4/2017 | Babiarz et al. |
| 2017/0145516 A1 | 5/2017 | Kopetz et al. |
| 2017/0159120 A1 | 6/2017 | Eijk et al. |
| 2017/0166962 A1 | 6/2017 | Eijk et al. |
| 2017/0211143 A1 | 7/2017 | Shendure et al. |
| 2017/0218459 A1 | 8/2017 | Talasaz et al. |
| 2017/0218460 A1 | 8/2017 | Talasaz |
| 2017/0226590 A1 | 8/2017 | Mortimer |
| 2017/0240972 A1 | 8/2017 | Mokhtari et al. |
| 2017/0240973 A1 | 8/2017 | Eltoukhy et al. |
| 2017/0260590 A1 | 9/2017 | Eltoukhy et al. |
| 2017/0342486 A1 | 11/2017 | Eijk et al. |
| 2018/0023125 A1 | 1/2018 | Talasaz et al. |
| 2018/0251848 A1 | 9/2018 | Diehn et al. |
| 2020/0013482 A1 | 1/2020 | Sikora |

FOREIGN PATENT DOCUMENTS

| | | |
|---|---|---|
| EP | 3178941 A1 | 6/2017 |
| WO | 2000058516 A2 | 10/2000 |
| WO | 2007037678 A2 | 4/2007 |
| WO | 2011091046 A1 | 7/2011 |
| WO | 2012014877 A1 | 2/2012 |
| WO | 2012129363 A2 | 9/2012 |
| WO | 2013019075 A2 | 2/2013 |
| WO | 2013060762 A1 | 5/2013 |
| WO | 2014039556 A1 | 3/2014 |
| WO | 2014149134 A2 | 9/2014 |
| WO | 2015100427 A1 | 7/2015 |
| WO | 2015175705 A1 | 11/2015 |
| WO | 2016109452 A1 | 7/2016 |
| WO | 2016179049 A1 | 11/2016 |
| WO | 2017015513 A1 | 1/2017 |
| WO | 2017062867 A1 | 4/2017 |
| WO | 2017062970 A1 | 4/2017 |

(56) References Cited

FOREIGN PATENT DOCUMENTS

| | | |
|---|---|---|
| WO | 2017106768 A1 | 6/2017 |
| WO | 2017136603 A1 | 8/2017 |
| WO | 2018064629 A1 | 4/2018 |

OTHER PUBLICATIONS

Fumagalli, Matteo. "Assessing the effect of sequencing depth and sample size in population genetics inferences." PloS one 8.11 (2013): e79667. (Year: 2013).*

Snyder, Matthew W., et al. "Cell-free DNA comprises an in vivo nucleosome footprint that informs its tissues-of-origin." Cell 164.1 (2016): 57-68. (Year: 2016).*

Paweletz, Cloud P., et al. "Bias-corrected targeted next-generation sequencing for rapid, multiplexed detection of actionable alterations in cell-free DNA from advanced lung cancer patients." Clinical Cancer Research 22.4 (2016): 915-922. (Year: 2015).*

"SliderII: High quality SNP calling using Illumina data at minimal coverage" (2009) Canada's Michael Smith Genome Sciences Centre.

Abbosh, C. et al. "Phylogenetic ctDNA analysis depicts early-stage lung cancer evolution" Nature (2017) 545(7655):446-451.

Agilent Protocol "SureSelect Target Enrichment System: Illumina Single-End Sequencing Platform Library Prep" Apr. 2009.

Albers, C.A. et al. "Dindel: Accurate indel calls from short-read data" Gen Research (2011) 21:961-973.

Alkan, et al. Personalized copy number and segmental duplication maps using next-generation sequencing. Nat Genet. Oct. 2009;41(10):1061-7. doi: 10.1038/ng.437. Epub Aug. 30, 2009.

Atanur, et al. The genome sequence of the spontaneously hypertensive rat: Analysis and functional significance. Genome Res. Jun. 2010;20(6):791-803. doi: 10.1101/gr. 103499.109. Epub Apr. 29, 2010.

Bonaldo, et al. Normalization and subtraction: two approaches to facilitate gene discovery. Genome Res. Sep. 1996;6(9):791-806.

Campbell, P.J. et al. "Subclonal phylogenetic structures in cancer revealed by ultra-deep sequencing" PNAS (2008) 105(35):13081-13086.

Carr, et al. Inferring relative proportions of DNA variants from sequencing electropherograms. Bioinformatics. Dec. 15, 2009;25(24):3244-50. doi: 10.1093/bioinformatics/btp583. Epub Oct. 9, 2009.

Castle, et al. DNA copy number, including telomeres and mitochondria, assayed using next-generation sequencing. BMC Genomics. Apr. 16, 2010;11:244. doi: 10.1186/1471-2164-11-244.

Chang, et al. Detection of allelic imbalance in ascitic supernatant by digital single nucleotide polymorphism analysis. Clin Cancer Res. Aug. 2002;8(8):2580-5.

Chmielecki, J. et al. "Targeted next-generation sequencing of DNA regions proximal to a conserved GXGXXG signaling motif enables systematic discovery of tyrosine kinase fusions in cancer" Nucleic Acids Res (2010) 38(20):6985-6996.

Clark, T.A. et al. "Analytical Validation of a Hybrid Capture Based Next-Generation Sequencing Clinical Assay for Genomic Profiling of Cell-Free Circulating Tumor DNA," J. Mol. Diagnostics (2018) 20(5):686-702.

Co-pending U.S. Appl. No. 14/039,168, filed Sep. 27, 2013.

Costello, et al. Discovery and characterization of artifactual mutations in deep coverage targeted capture sequencing data due to oxidative DNA damage during sample preparation. Nucleic Acids Res. Apr. 1, 2013;41(6):e67. doi: 10.1093/nar/gks1443. Epub Jan. 8, 2013.

Craig, et al. Identification of genetic variants using bar-coded multiplexed sequencing. Nat Methods. Oct. 2008;5(10):887-893. doi: 10.1038/nmeth.1251. Epub Sep. 14, 2008. Supplementary Info.

Craig, et al. Identification of genetic variants using bar-coded multiplexed sequencing. Nat Methods. Oct. 2008;5(10):887-93. doi: 10.1038/nmeth.1251. Epub Sep. 14, 2008.

Cummings, N. et al. "Combining target enrichment with barcode multiplexing for high throughput SNP discovery" BMC Genomics (2010) 11:641.

Daines, et al. High-throughput multiplex sequencing to discover copy number variants in Drosophila. Genetics. Aug. 2009;182(4):935-41. doi: 10.1534/genetics.109.103218. Epub Jun. 15, 2009.

Ellison et al. EGFR mutation testing in lung ancer: a review of available methods and their use for analysis of tumour issue and cytology samples Journal of Clinical Pathology vol. 66, pp. 79-89 (2013).

Extended European search report and opinion dated Feb. 5, 2021 for EP Application No. 20203923.6.

Extended European search report and opinion for EP Application No. 17857586.6 dated Apr. 26, 2019.

Fan, et al. Non-invasive prenatal measurement of the fetal genome. Nature. Jul. 19, 2012;487(7407):320-4. doi: 10.1038/nature 11251.

Forbes, S.A. et al. "COSMIC: mining complete cancer genomes in the Catalogue of Somatic Mutations in Cancer" Nucleic Acids Res (2010) 39:D945-D950.

Forbes, S.A. et al. "The Catalogue of Somatic Mutations in Cancer (COSMIC)" Current Prot Human Genet (2008) 10.11.1-10.11.26.

Garber, K. "Fixing the front end" Nature Biotech (2008) 26(10):1101-1104.

Gnirke et al. Solution hybrid selection with ultra-long oligonucleotides for maddively parallel targeted sequencing Nature Biotechnology vol. 27, pp. 182-189 (2009).

Grant, et al. SNP genotyping on a genome-wide amplified DOP-PCR template. Nucleic Acids Res. Nov. 15, 2002;30(22):e25.

Grimm, D. et al. "Accurate indel prediction using paired-end short reads" BMC Genomics (2013) 14:132 (10 pages).

Gundry, et al. "Direct mutation analysis by high-throughput sequencing: from gremlin to low-abundant, somatic variants" Mutat Res Jan. 3, 2012; 729(1-2):1-15. doi: 10.1016/mrfmmm.2011.10.001. Pub Oct. 12, 2011.

Gundry, et al. Direct, genome-wide assessment of DNA mutations in single cells. Nucleic Acids Res. Mar. 2012;40(5):2032-40. doi: 10.1093/nar/gkr949. Epub Nov. 15, 2011.

Hamady, et al. Error-correcting barcoded primers for pyrosequencing hundreds of samples in multiplex. Nat Methods. Mar. 2008;5(3):235-7. doi: 10.1038/nmeth.1184. Epub Feb. 10, 2008.

Hensel, et al. Simultaneous identification of bacterial virulence genes by negative selection. Science. Jul. 21, 1995;269(5222):400-3.

Hiatt, et al. Single molecule molecular inversion probes for targeted, high-accuracy detection of low-frequency variation. Genome Res. May 2013;23(5):843-54. doi: 10.1101/gr.147686.112. Epub Feb. 4, 2013.

International search report and written opinion dated Feb. 22, 2018 for PCT/US2017/054607.

Jakubek, et al., A model of binding on DNA microarrays: understanding the combined effect of probe synthesis failure, cross-hybridization, DNA fragmentation and other experimental details of affymetrix arrays, Jakubek and Cutler BMC Genomics 2012, 13:737, 13 pages.

Kenny, E.M. et al. "Multiplex Target Enrichment Using DNA Indexing for Ultra-High Throughput SNP Detection" DNA Res (2010) 18:31-38.

Koboldt, D.C. et al. "Challenges of sequencing human genomes" Briefings in Bioinformatics (2010) 5:484-498.

Kukita, Y. et al. "High-fidelity target sequencing of individual molecules identified using barcode sequences: de novo detection and absolute quantitation of mutations in plasma cell-free DNA from cancer patients" DNA Research (2015) 22(4):269-277.

Lanman, et al., Analytical and Clinical Validation of a Digital Sequencing Panel for Quantitative, Highly Accurate Evaluation of Cell-Free Circulating Tumor DNA PLoS One, Oct. 2015, 10(10), e0140712. doi:10.1371/journal.pone.0140712.

Ley, T.J. et al. "DNA sequencing of a cytogenetically normal acute myeloid leukaemia genome" Nature (2008) 456:66-72.

Ley, T.J. et al. "DNA sequencing of a cytogenetically normal acute myeloid leukaemia genome" Nature (2008) 456:66-72; Supplementary Info 1.

(56) References Cited

OTHER PUBLICATIONS

Li, H. "NGS alignment programs" (2009) http://lh3lh3.users.sourceforge.net/NGSalign.shtml.
Li, H. et al., "Fast and accurate short read alignment with Burrows-Wheeler transform," Bioinformatics 2009, 25(14), 1754-1760.
Lizardi, et al. Mutation detection and single-molecule counting using isothermal rolling-circle amplification. Nat Genet. Jul. 1998;19(3):225-32.
Lo, Y.M.D. et al. "Maternal Plasma DNA Sequencing Reveals the Genome-Wide Genetic and Mutational Profile of the Fetus," Sci Transl Med (2010) 2(61):1-13.
Makrigiorgos, et al., A PCR-Based amplification method retaining quantative difference between two complex genomes. Nature Biotech, vol. 20, No. 9, pp. 936-939 (Sep. 2002).
Malhis, N. et al. "High quality SNP calling using Illumina data at shallow coverage" Bioinformatics (2010) 26(8):1029-1035.
Mamanova, L. et al., "Target-enrichment strategies for next-generation sequencing," Nat. Methods 2010, 7(2), 111-118.
Mardis, E.R. et al. "Recurring Mutations Found by Sequencing an Acute Myeloid Leukemia Genome" New Engl J Med (2009) 361:1058-1066.
Marsh, S. et al. "Pharmacogenetic analysis of paclitaxel transport and metabolism genes in breast cancer" Pharmacogenomics J (2007) 7:362-365.
Medvedev, et al. Detecting copy number variation with mated short reads. Genome Res. Nov. 2010;20(11):1613-22. doi: 10.1101/gr.106344.110. Epub Aug. 30, 2010.
Mei, et al. Identification of recurrent regions of Copy-Number Variants across multiple individuals. BMC Bioinformatics. Mar. 22, 2010;11:147. doi: 10.1186/1471-2105-11-147.
Metzker, M.L. "Sequencing technologies—the next generation" Nature Reviews Genetics (2010) 11:31-46.
Newman, et al. An ultrasensitive method for quantitating circulating tumor DNA with broad patient coverage. Nat Med. May 2014;20(5):548-54. doi: 10.1038/nm.3519. Epub Apr. 6, 2014.
Non-Final Office Action in U.S. Appl. No. 16/338,445, dated Jul. 8, 2022.
Office Action dated Nov. 16, 2021 for U.S. Appl. No. 17/383,385.
Office Action for Canadian Application No. 3027919 dated Feb. 19, 2019.
Office Action for Canadian Application No. 3027919 dated Aug. 27, 2019.
Office Action for Canadian Application No. 3027919 dated Apr. 7, 2021.
Office Action for Japanese Patent Application No. 2018-568202 dated Jul. 29, 2020.
Office action for U.S. Appl. No. 17/383,385 dated Mar. 7, 2022.
Ogino, et al. Quantification of PCR bias caused by a single nucleotide polymorphism in SMN gene dosage analysis. J Mol Diagn. Nov. 2002;4(4):185-90.
Park, et al. Discovery of common Asian copy number variants using integrated high-resolution array CGH and massively parallel DNA sequencing. Nat Genet. May 2010;42(5):400-5. doi: 10.1038/ng.555. Epub Apr. 4, 2010.
Paweletz, C.P. et al. "Bias-corrected targeted next-generation sequencing for rapid, multiplexed detection of actionable alterations in cell-free DNA from advanced lung cancer patients" Clin Canc Res (2016) 22(4):915-922.
Phallen, J. et al. "Direct detection of early-stage cancers using circulating tumor DNA" Sci Trans Med (2017) vol. 9, Issue 403, eaan2415DOI: 10.1126/scitranslmed.aan2415.
Pleasance, et al. A small-cell lung cancer genome with complex signatures of tobacco exposure. Nature. Jan. 14, 2010;463(7278):184-90. doi: 10.1038/nature08629. Epub Dec. 16, 2009.
Roy, L. et al. "Survival advantage from imatinib compared with the combination interferon-plus cytarabine in chronic-phase chronic myelogenous leukemia: historical comparison between two phase 3 trials" Blood (2006) 108(5):1478-1484.
Schmitt et al. Supplemental Information http://www.pnas.org/content/suppl/2012/08/01/1208715109.DCSupplemental (2012).
Schmitt, et al. Detection of ultra-rare mutations by next-generation sequencing. Proc Natl Acad Sci U S A. Sep. 4, 2012;109(36):14508-13. doi: 10.1073/pnas.1208715109. Epub Aug. 1, 2012.
Search Report and Written Opinion for Singapore Patent Application No. 11201811159S dated Jul. 7, 2020.
Simpson, et al. Copy number variant detection in inbred strains from short read sequence data. Bioinformatics. Feb. 15, 2010;26(4):565-7. doi: 10.1093/bioinformatics/btp693. Epub Dec. 18, 2009.
Singer, S et al. "Nelder-Mead algorithm" Scholarpedia (2009) vol. 4, Article 2928, 9 pages.
Statham, et al. "Genome-wide nucleosome occupancy and DNA methylation profiling of four human cell lines" Genomics Data (Mar. 2015) 3:94-96.
Stephens, P.J. et al. "Complex landscapes of somatic rearrangement in human breast cancer genomes" Nature 462:1005-1010.
Stevens, et al., DNA hybridization on microparticles; determining capture-probe density and equilibrium dissociation constants, Nucleic Acids Research, 1999, 27(7):1719-27.
Stratton, M.R. et al. "The cancer genome" Nature (2009) 458:719-724.
Tan, et al. Genome-wide comparison of DNA hydroxymethylation in mouse embryonic stem cells and neural progenitor cells by a new comparative hMeDIP-seq method. Nucleic Acids Res. Apr. 2013;41(7):e84. doi: 10.1093/nar/gkt091. Epub Feb. 13, 2013.
Taudien, et al. Haplotyping and copy number estimation of the highly polymorphic human beta-defensin locus on Bp23 by 454 amplicon sequencing. BMC Genomics. Apr. 19, 2010;11:252. doi: 10.1186/1471-2164-11-252.
Tewhey, R. et al. "Enrichment of sequencing targets from the human genome by solution hybridization" Genome Biology (2009) 10:R116 (13 pages).
Tomaz, et al. Differential methylation as a cause of allele dropout at the imprinted GNAS locus. Genet Test Mol Biomarkers. Aug. 2010;14(4):455-60. doi: 10.1089/gtmb.2010.0029.
Van der Auwera, G.A. et al. "From FastQ Data to High-Confidence Variant Calls: The Genome Analysis Toolkit Best Practices Pipeline" Curr Protocols in Bioinformatics (2013) 11.10.1-11.10.33.
Walker, et al. Isothermal in vitro amplification of DNA by a restriction enzyme/DNA polymerase system. Proc Natl Acad Sci U S A. Jan. 1, 1992;89(1):392-6.
Walsh, et al. Detection of inherited mutations for breast and ovarian cancer using genomic capture and massively parallel sequencing. Proc Natl Acad Sci U S A. Jul. 13, 2010;107(28):12629-33. doi: 10.1073/pnas.1007983107. Epub Jun. 28, 2010.
Weber, et al. A real-time polymerase chain reaction assay for quantification of allele ratios and correction of amplification bias. Anal Biochem. Sep. 15, 2003;320(2):252-8.
Willems, T. et al. "Population—Scale Sequencing Data Enable Precise Estimates of Y-STR Mutation Rates" Am J Human Genetics (2016) 98:919-933.
Willems, T. et al. "The landscape of human STR variation" Genome Research (2014) 24:1894-1904.
Wojdacs, et al. Primer design versus PCR bias in methylation independent PCR amplifications. Epigenetics. May 16, 2009;4(4):231-4. Epub May 14, 2009.
Wood, et al. Using next-generation sequencing for high resolution multiplex analysis of copy number variation from nanogram quantities of DNA from formalin-fixed paraffin-embedded specimens. Nucleic Acids Res. Aug. 2010;38(14):e151. doi: 10.1093/nar/gkq510. Epub Jun. 4, 2010.
Yandell, et al. A probabilistic disease-gene finder for personal genomes. Genome Res. Sep. 2011;21(9):1529-42. doi: 10.1101/gr.123158.111. Epub Jun. 23, 2011.
Yassour, M. et al. "Ab initio construction of a eukaryotic transcriptome by massively parallel mRNA sequencing" Nature (2009) 106(9):3264-3269.
Yoon, et al. Sensitive and accurate detection of copy number variants using read depth of coverage. Genome Res. Sep. 2009;19(9):1586-92. doi: 10.1101/gr.092981.109. Epub Aug. 5, 2009.
Zhang, et al. The impact of next-generation sequencing on genomics. J Genet Genomics. Mar. 20, 2011;38(3):95-109. doi: 10.1016/j.jgg 2011.02.003. Epub Mar. 15, 2011.

(56) References Cited

OTHER PUBLICATIONS

Opponents (Margaret Dixon Limited) Grounds for Appeal in EP3461274, Appeal No. T0364/23-33.08, dated Apr. 21, 2023.
Snyder, M.W. et al. "Cell-free DNA Comprises an In Vivo Nucleosome Footprint that Informs Its Tissues-Of-Origin" Cell (2016) 164:57-68 & Supplemental Information.
Chinese Office Action for Chinese Application No. 2017800491359 dated Jul. 30, 2023.
Ivanov, M. et al. "Non-random fragmentation patterns in circulating cell-free DNA reflect epigenetic regulation" BMC Genomics (2015) 16(Suppl. 13):51.

* cited by examiner

METHODS FOR MULTI-RESOLUTION ANALYSIS OF CELL-FREE NUCLEIC ACIDS

CROSS-REFERENCE

This application is a continuation of U.S. patent application Ser. No. 18/055,298 filed Nov. 14, 2022, which is a continuation of U.S. patent application Ser. No. 17/383,385 filed Jul. 22, 2021, which is a continuation of U.S. patent application Ser. No. 16/338,445, filed Mar. 29, 2019, which is a U.S. national stage application of International Patent Application No. PCT/US2017/054607, filed Sep. 29, 2017, which claims priority to U.S. Provisional Application No. 62/402,940, filed Sep. 30, 2016, U.S. Provisional Application No. 62/468,201, filed Mar. 7, 2017, and U.S. Provisional Application No. 62/489,391, filed Apr. 24, 2017, each of which is entirely incorporated herein by reference.

SEQUENCE LISTING

The instant application contains a Sequence listing which has been submitted electronically in ASCII format and is hereby incorporated by reference in its entirety. Said ASCII copy, created Sep. 27, 2017, is named 42534-733_601_SL.txt and is 2,938 bytes in size.

BACKGROUND

Analysis of cell-free nucleic acids (e.g., deoxyribonucleic acid or ribonucleic acid) for tumor-derived genetic variants is a critical step in a typical analysis pipeline for cancer detection, assessment, and monitoring applications. Most current methods of cancer diagnostic assays of cell-free nucleic acids focus on the detection of tumor-related somatic variants, including single-nucleotide variants (SNVs), copy-number variations (CNVs), fusions, and insertions/deletions (indels), which are all mainstream targets for liquid biopsy. A typical analysis approach may comprise enriching a nucleic acid sample for targeted regions of a genome, followed by sequencing of enriched nucleic acids and analysis of sequence read data for genetic variants of interest. These nucleic acids may be enriched using a bait mixture selected for a particular assay according to assay constraints, including limited sequencing load and utility associated with each genomic region of interest.

SUMMARY

In an aspect, the present disclosure provides a bait set panel comprising one or more bait sets that selectively enrich for one or more nucleosome-associated regions of a genome, said nucleosome-associated regions comprising genomic regions having one or more genomic base positions with differential nucleosomal occupancy, wherein the differential nucleosomal occupancy is characteristic of a cell or a tissue type of origin or a disease state.

In some embodiments, each of the one or more nucleosome-associated regions of a bait set panel comprise at least one of: (i) significant structural variation, comprising a variation in nucleosomal positioning, said structural variation selected from the group consisting of: an insertion, a deletion, a translocation, a gene rearrangement, methylation status, a micro-satellite, a copy number variation, a copy number-related structural variation, or any other variation which indicates differentiation; and (ii) instability, comprising one or more significant fluctuations or peaks in a genome partitioning map indicating one or more locations of nucleosomal map disruptions in a genome.

In some embodiments, the one or more bait sets of a bait set panel are configured to capture nucleosome-associated regions of the genome based on a function of a plurality of reference nucleosomal occupancy profiles (i) associated with one or more disease states and one or more non-disease states; (ii) associated with a known somatic mutation, such as SNV, CNV, indel, or re-arrangement; and/or (iii) associated with differential expression patterns. In an embodiment, the one or more bait sets of a bait set panel selectively enrich for one or more nucleosome-associated regions in a cell-free deoxyribonucleic acid (cfDNA) sample.

In another aspect, the present disclosure provides a method for enriching a nucleic acid sample for nucleosome-associated regions of a genome comprising (a) bringing a nucleic acid sample in contact with a bait set panel, said bait set panel comprising one or more bait sets that selectively enrich for one or more nucleosome-associated regions of a genome; and (b) enriching the nucleic acid sample for one or more nucleosome-associated regions of a genome.

In some embodiments, the one or more bait sets in a bait set panel are configured to capture nucleosome-associated regions of the genome based on a function of a plurality of reference nucleosomal occupancy profiles associated with one or more disease states and one or more non-disease states. In an embodiment, the one or bait sets in a bait set panel selectively enrich for the one or more nucleosome-associated regions in a cfDNA sample. In an embodiment, the method for enriching a nucleic acid sample for nucleosome-associated regions of a genome further comprises sequencing the enriched nucleic acids to produce sequence reads of the nucleosome-associated regions of a genome.

In another aspect, the present disclosure provides a method for generating a bait set comprising (a) identifying one or more regions of a genome, said regions associated with a nucleosome profile, and (b) selecting a bait set to selectively capture said regions. In an embodiment, a bait set in a bait set panel selectively enriches for one or more nucleosome-associated regions in a cell-free deoxyribonucleic acid sample.

In another aspect, the present disclosure provides a bait panel comprising a first bait set that selectively hybridizes to a first set of genomic regions of a nucleic acid sample comprising a predetermined amount of DNA, which is provided at a first concentration ratio that is less than a saturation point of the first bait set; and a second bait set that selectively hybridizes to a second set of genomic regions of the nucleic acid sample, which is provided at a second concentration ratio that is associated with a saturation point of the second bait set. In an embodiment, the first set of genomic regions comprises one or more backbone genomic regions and the second set of genomic regions comprises one or more hotspot genomic regions.

In another aspect, the present disclosure provides a method for enriching for multiple genomic regions comprising bringing a predetermined amount of a nucleic acid sample in contact with a bait panel comprising (i) a first bait set that selectively hybridizes to a first set of genomic regions of the nucleic acid sample, provided at a first concentration ratio that is less than a saturation point of the first bait set, and (ii) a second bait set that selectively hybridizes to a second set of genomic regions of the nucleic acid sample, provided at a second concentration ratio that is associated with a saturation point of the second bait set; and enriching the nucleic acid sample for the first set of genomic regions and the second set of genomic regions.

In some embodiments, the method further comprises sequencing the enriched nucleic acids to produce sequence reads of the first set of genomic regions and the second set of genomic regions.

In some embodiments, the saturation point of a bait set is determined by (a) for each of the baits in the bait set, generating a titration curve comprising (i) measuring the capture efficiency of the bait as a function of the concentration of the bait, and (ii) identifying an inflection point within the titration curve, thereby identifying a saturation point associated with the bait; and (b) selecting a saturation point that is larger than substantially all of the saturation points associated with baits in the bait set, thereby determining the saturation point of the bait set.

In some embodiments, the capture efficiency of a bait is determined by (a) providing a plurality of nucleic acid samples obtained from a plurality of subjects in a cohort; (b) hybridizing the bait with each of the nucleic acid samples, at each of a plurality of concentrations of the bait; (c) enriching with the bait, a plurality of genomic regions of the nucleic acid samples, at each of the plurality of concentrations of the bait; and (d) measuring number of unique nucleic acid molecules or nucleic acid molecules with representation of both strands of an original double-stranded nucleic acid molecule representing the capture efficiency at each of the plurality of concentrations of the bait.

In some embodiments, an inflection point is a first concentration of the bait such that observed capture efficiency does not increase significantly at concentrations of the bait greater than the first concentration. An inflection point may be a first concentration of the bait such that an observed increase between (1) the capture efficiency at a bait concentration of twice the first concentration compared to (2) the capture efficiency at the first bait concentration, is less than about 1%, less than about 2%, less than about 3%, less than about 4%, less than about 5%, less than about 6%, less than about 7%, less than about 8%, less than about 9%, less than about 10%, less than about 12%, less than about 14%, less than about 16%, less than about 18%, or less than about 20%.

In some embodiments, the nucleic acid sample comprises a cell-free nucleic acid sample. In an embodiment, a method for enriching for multiple genomic regions further comprises sequencing the enriched nucleic acid sample to produce a plurality of sequence reads. In an embodiment, a method for enriching for multiple genomic regions further comprises producing an output comprising a nucleic acid sequence representative of the nucleic acid sample.

In another aspect, the present disclosure provides a bait panel comprising a first set that selectively captures backbone regions of a genome, said backbone regions associated with a ranking function of sequencing load and utility, wherein the ranking function of each backbone region has a value less than a predetermined threshold value; and a second bait set that selectively captures hotspot regions of a genome, said hotspot regions associated with a ranking function of sequencing load and utility, wherein the ranking function of each hotspot region has a value greater than or equal to the predetermined threshold value.

In some embodiments, the hotspot regions comprise one or more nucleosome informative regions, said nucleosome informative regions comprising a region of maximum nucleosome differentiation. In an embodiment, the bait panel further comprises a second bait set that selectively captures disease informative regions. In an embodiment, the baits in the first bait set are at a first relative concentration to the bait panel, and the baits in the second bait set are at a second relative concentration to the bait panel.

In another aspect, the present disclosure provides a method for generating a bait set comprising identifying one or more backbone genomic regions of interest, wherein the identifying the one or more backbone genomic regions comprises maximizing a ranking function of sequencing load and utility associated with each of the backbone genomic regions; identifying one or more hot-spot genomic regions of interest; creating a first bait set that selectively captures the backbone genomic regions of interest; and creating a second bait set that selectively captures the hot-spot genomic regions of interest, wherein the second bait set has a higher capture efficiency than the first bait set.

In some embodiments, the one or more hot-spots are selected using one or more of the following: (i) maximizing a ranking function of sequencing load and utility associated with each of the hot-spot genomic regions, (ii) nucleosome profiling across the one or more genomic regions of interest, (iii) predetermined cancer driver mutations or prevalence across a relevant patient cohort, and (iv) empirically identified cancer driver mutations.

In some embodiments, identifying one or more hotspots of interest comprises using a programmed computer processor to rank a set of hot-spot genomic regions based on a ranking function of sequencing load and utility associated with each of the hot-spot genomic regions. In some embodiments, identifying the one or more backbone genomic regions of interest comprises ranking a set of backbone genomic regions based on a ranking function of sequencing load and utility associated with each of the backbone genomic regions of interest. In some embodiments, identifying the one or more hot-spot genomic regions of interest comprises utilizing a set of empirically determined minor allele frequency (MAF) values or clonality of a variant measured by its MAF in relationship to the highest presumed driver or clonal mutation in a sample.

In some embodiments, sequencing load of a genomic region is calculated by multiplying together one or more of (i) size of the genomic region in base pairs, (ii) relative fraction of reads spent on sequencing fragments mapping to the genomic region, (iii) relative coverage as a result of sequence bias of the genomic region, (iv) relative coverage as a result of amplification bias of the genomic region, and (v) relative coverage as a result of capture bias of the genomic region.

In some embodiments, utility of a genomic region is calculated by multiplying together one or more of (i) frequency of one or more actionable mutations in the genomic region, (ii) frequency of one or more mutations associated with above-average minor allele frequencies (MAFs) in the genomic region, (iii) fraction of patients in a cohort harboring a somatic mutation within the genomic region, (iv) sum of MAF for variants in patients in a cohort, said patients harboring a somatic mutation within the genomic region, and (v) ratio of (1) MAF for variants in patients in a cohort, said patients harboring a somatic mutation within the genomic region, to (2) maximum MAF for a given patient in the cohort.

In some embodiments, actionable mutations comprise one or more of (i) druggable mutations, (ii) mutations for therapeutic monitoring, (iii) disease specific mutations, (iv) tissue specific mutations, (v) cell type specific mutations, (vi) resistance mutations, and (vii) diagnostic mutations. In an embodiment, mutations associated with higher minor allele frequencies comprise one or more driver mutations or are known from external data or annotation sources.

In another aspect, the present disclosure provides a bait panel comprising a plurality of bait sets, each bait set (i) comprising one or more baits that selectively capture one or more genomic regions with utility in the same quantile across the plurality of baits, and (ii) having a different relative concentration from each of the other bait sets with utility in a different quantile across the plurality of baits.

In another aspect, the present disclosure provides a method of selecting a set of panel blocks comprising (a) for each panel block, (i) calculating a utility of the panel block, (ii) calculating a sequencing load of the panel block, and (iii) calculating a ranking function of the panel block; and (b) performing an optimization process to select a set of panel blocks that maximizes the total ranking function values of the selected panel blocks.

In some embodiments, a ranking function of a panel block is calculated as the utility of a panel block divided by the sequencing load of a panel block. In some embodiments, the combinatorial optimization process comprises a greedy algorithm.

In another aspect, the present disclosure provides a method comprising (a) providing a plurality of bait mixtures, wherein each bait mixture comprises a first bait set that selectively hybridizes to a first set of genomic regions and a second bait set that selectively hybridizes to a second set of genomic regions, and wherein the bait mixtures comprise the first bait set at different concentrations and the second bait set at the same concentrations; (b) contacting each bait mixture with a nucleic acid sample to capture nucleic acid from the sample with the bait sets, wherein the nucleic acid samples have a nucleic acid concentration around the saturation point of the second bait set; (c) sequencing the nucleic acids captured with each bait mixture to produce sets of sequence reads; (d) determining the relative number of sequence reads for the first set of genomic regions and the second set of genomic regions for each bait mixture; and (e) identifying at least one bait mixture that provides read depths for the second set of genomic regions and, optionally, first set of genomic regions, at predetermined amounts.

In another aspect, the present disclosure provides a method for improving accuracy of detecting an insertion or deletion (indel) from a plurality of sequence reads derived from cell-free deoxyribonucleic acid (cfDNA) molecules in a bodily sample of a subject, which plurality of sequence reads are generated by nucleic acid sequencing, comprising (a) for each of the plurality of sequence reads associated with the cell-free DNA molecules, providing: a predetermined expectation of an indel being detected in one or more sequence reads of the plurality of sequence reads; a predetermined expectation that a detected indel is a true indel present in a given cell-free DNA molecule of the cell-free DNA molecules, given that an indel has been detected in the one or more of the sequence reads; and a predetermined expectation that a detected indel is introduced by non-biological error, given that an indel has been detected in the one or more of the sequence reads; (b) providing quantitative measures of one or more model parameters characteristic of sequence reads generated by nucleic acid sequencing; (c) detecting one or more candidate indels in the plurality of sequence reads associated with the cell-free DNA molecules; and (d) for each candidate indel, performing a hypothesis test using one or more of the model parameters to classify said candidate indel as a true indel or an introduced indel, thereby improving accuracy of detecting an indel.

In another aspect, the present disclosure provides a kit comprising (a) a sample comprising a predetermined amount of DNA; and (b) a bait set panel comprising (i) a first bait set that selectively hybridizes to a first set of genomic regions of a nucleic acid sample comprising a predetermined amount of DNA, provided at a first concentration ratio that is less than a saturation point of the first bait set and (ii) a second bait set that selectively hybridizes to a second set of genomic regions of the nucleic acid sample, provided at a second concentration ratio that is associated with a saturation point of the second bait set.

In some embodiments, the method for improving accuracy of detecting an insertion or deletion (indel) from a plurality of sequence reads derived from cell-free deoxyribonucleic acid (cfDNA) molecules in a bodily sample of a subject further comprises enriching one or more loci from the cell-free DNA in the bodily sample before step (a), thereby producing enriched polynucleotides.

In some embodiments, the method further comprises amplifying the enriched polynucleotides to produce families of amplicons, wherein each family comprises amplicons originating from a single strand of the cell-free DNA molecules. In some embodiments, the non-biological error comprises error in sequencing at a plurality of genomic base locations. In some embodiments, the non-biological error comprises error in amplification at a plurality of genomic base locations.

In some embodiments, model parameters comprise one or more of (e.g., one or more of, two or more of, three or more of, or four of) (i) for each of one or more variant alleles, a frequency of the variant allele ($\alpha$) and a frequency of non-reference alleles other than the variant allele ($\alpha'$); (ii) a frequency of an indel error in the entire forward strand of a family of strands ($\beta_1$), wherein a family comprises a collection of amplicons originating from a single strand of the cell-free DNA molecules; (iii) a frequency of an indel error in the entire reverse strand of a family of strands ($\beta_2$); and (iv) a frequency of an indel error in a sequence read ($\gamma$).

In some embodiments, the step of performing a hypothesis test comprises performing a multi-parameter maximization algorithm. In some embodiments, the multi-parameter maximization algorithm comprises a Nelder-Mead algorithm. In an embodiment, the classifying of a candidate indel as a true indel or an introduced indel comprises (a) maximizing a multi-parameter likelihood function, (b) classifying a candidate indel as a true indel if the maximum likelihood function value is greater than a predetermined threshold value, and (c) classifying a candidate indel as an introduced indel if the maximum likelihood function value is less than or equal to a predetermined threshold value.

In another aspect, the present disclosure provides a non-transitory computer-readable medium comprising machine executable code that, upon execution by one or more computer processors, implements a method for generating a bait set comprises identifying one or more backbone genomic regions of interest, wherein the identifying the one or more backbone genomic regions comprises maximizing a ranking function of sequencing load and utility associated with each of the backbone genomic regions; identifying one or more hot-spot genomic regions of interest; creating a first bait set that selectively captures the backbone genomic regions of interest; and creating a second bait set that selectively captures the hot-spot genomic regions of interest, wherein the second bait set has a higher capture efficiency than the first bait set.

In another aspect, the present disclosure provides a non-transitory computer-readable medium comprising machine executable code that, upon execution by one or more computer processors, implements a method of selecting a set of panel blocks comprises (a) for each panel block, (i) calculating a utility of the panel block, (ii) calculating a sequencing load of the panel block, and (iii) calculating a ranking function of the panel block; and (b) performing an optimization process to select a set of panel blocks that maximizes the total ranking function values of the selected panel block.

In another aspect, the present disclosure provides a non-transitory computer-readable medium comprising machine executable code that, upon execution by one or more computer processors, implements a method for improving accuracy of detecting an insertion or deletion (indel) from a plurality of sequence reads derived from cell-free deoxyribonucleic acid (cfDNA) molecules in a bodily sample of a subject, which plurality of sequence reads are generated by nucleic acid sequencing, comprises (a) for each of the plurality of sequence reads associated with the cell-free DNA molecules, providing: a predetermined expectation of an indel being detected in one or more sequence reads of the plurality of sequence reads; a predetermined expectation that a detected indel is a true indel present in a given cell-free DNA molecule of the cell-free DNA molecules, given that an indel has been detected in the one or more of the sequence reads; and a predetermined expectation that a detected indel is introduced by non-biological error, given that an indel has been detected in the one or more of the sequence reads; (b) providing quantitative measures of one or more model parameters characteristic of sequence reads generated by nucleic acid sequencing; (c) detecting one or more candidate indels in the plurality of sequence reads associated with the cell-free DNA molecules; and (d) for each candidate indel, performing a hypothesis test using one or more of the model parameters to classify said candidate indel as a true indel or an introduced indel, thereby improving accuracy of detecting an indel.

In another aspect, the present disclosure provides a method for enriching for multiple genomic regions, comprising: (a) bringing a predetermined amount of nucleic acid from a sample in contact with a bait mixture comprising (i) a first bait set that selectively hybridizes to a first set of genomic regions of the nucleic acid from the sample, which first bait set is provided at a first concentration that is less than a saturation point of the first bait set, and (ii) a second bait set that selectively hybridizes to a second set of genomic regions of the nucleic acid sample, which second bait set is provided at a second concentration that is associated with a saturation point of the second bait set; and (b) enriching the nucleic acid sample for the first set of genomic regions and the second set of genomic regions.

In some embodiments, the second bait set has a saturation point that is larger than substantially all of the saturation points associated with baits in the second bait set when a bait of the second bait set is subjected to a titration curve generated by (i) measuring the capture efficiency of a bait of the second bait set as a function of the concentration of the bait, and (ii) identifying an inflection point within the titration curve, thereby identifying a saturation point associated with the bait. In some embodiments, the saturation point is selected such that an observed capture efficiency increases by less than 20% at a concentration of the bait twice that of the first concentration.

In some embodiments, the saturation point is selected such that an observed capture efficiency increases by less than 10% at a concentration of the bait twice that of the first concentration. In some embodiments, the saturation point is selected such that an observed capture efficiency increases by less than 5% at a concentration of the bait twice that of the first concentration. In some embodiments, the saturation point is selected such that an observed capture efficiency increases by less than 2% at a concentration of the bait twice that of the first concentration. In some embodiments, the saturation point is selected such that an observed capture efficiency increases by less than 1% at a concentration of the bait twice that of the first concentration.

In some embodiments, the first bait set or the second bait set selectively enrich for one or more nucleosome-associated regions of a genome, said nucleosome-associated regions comprising genomic regions having one or more genomic base positions with differential nucleosomal occupancy, wherein the differential nucleosomal occupancy is characteristic of a cell or tissue type of origin or disease state. In some embodiments, the nucleic acid sample comprises a cell-free nucleic acid sample. In some embodiments, the method further comprises: (c) sequencing the enriched nucleic acid sample to produce a plurality of sequence reads. In some embodiments, the method further comprises: (d) producing an output comprising a nucleic acid sequence representative of the nucleic acid sample.

In another aspect, the present disclosure provides a method for generating a bait set comprising: (a) identifying one or more predetermined backbone genomic regions, wherein the identifying the one or more backbone genomic regions comprises maximizing a ranking function of sequencing load and utility associated with each of the backbone genomic regions; (b) identifying one or more predetermined hot-spot genomic regions, wherein the one or more hot-spots are selected using one or more of the following: (i) maximizing a ranking function of sequencing load and utility associated with each of the hot-spot genomic regions, (ii) nucleosome profiling across the one or more predetermined genomic regions, (iii) predetermined cancer driver mutations or prevalence across a relevant patient cohort, and (iv) empirically identified cancer driver mutations; (c) creating a first bait set that selectively captures the predetermined backbone genomic regions; and (d) creating a second bait set that selectively captures the predetermined hotspot genomic regions, wherein the second bait set has a higher capture efficiency than the first bait set. In some embodiments, a predetermined region (e.g., a predetermined backbone region or a predetermined hotspot region) is a region of interest (e.g., a backbone region of interest or a hotspot region of interest, respectively).

In some embodiments, the identifying the one or more predetermined hotspots comprises using a programmed computer processor to rank a set of hotspot genomic regions based on a ranking function of sequencing load and utility associated with each of the hotspot genomic regions. In some embodiments, the identifying the one or more predetermined backbone genomic regions comprises: (i) ranking a set of backbone genomic regions based on a ranking function of sequencing load and utility associated with each of the predetermined backbone genomic regions; (ii) utilizing a set of empirically determined minor allele frequency (MAF) values or clonality of a variant measured by its MAF in relationship to the highest presumed driver or clonal mutation in a sample; or (iii) a combination of (i) and (ii).

In some embodiments, the sequencing load of a genomic region is calculated by multiplying together one or more of: (i) size of the genomic region in base pairs, (ii) relative fraction of reads spent on sequencing fragments mapping to the genomic region, (iii) relative coverage as a result of sequence bias of the genomic region, (iv) relative coverage as a result of amplification bias of the genomic region, and (v) relative coverage as a result of capture bias of the genomic region. In some embodiments, the utility of a genomic region is calculated by multiplying together one or more of: (i) frequency of one or more actionable mutations in the genomic region, (ii) frequency of one or more mutations associated with above-average minor allele frequencies (MAFs) in the genomic region, (iii) fraction of patients in a cohort harboring a somatic mutation within the genomic region, (iv) sum of MAF for variants in patients in a cohort, said patients harboring a somatic mutation within the genomic region, and (v) ratio of (1) MAF for variants in patients in a cohort, said patients harboring a somatic mutation within the genomic region, to (2) maximum MAF for a given patient in the cohort.

In some embodiments, the actionable mutations comprise one or more of: (i) druggable mutations, (ii) mutations for therapeutic monitoring, (iii) disease specific mutations, (iv) tissue specific mutations, (v) cell type specific mutations, (vi) resistance mutations, and (vii) diagnostic mutations. In some embodiments, the mutations associated with higher minor allele frequencies comprise one or more driver mutations or are known from external data or annotation sources.

In another aspect, the present disclosure provides a method comprising: (a) providing a plurality of bait mixtures, wherein each bait mixture comprises a first bait set that selectively hybridizes to a first set of genomic regions and a second bait set that selectively hybridizes to a second set of genomic regions, and wherein the bait mixtures comprise the first bait set at different concentrations and the second bait set at the same concentrations; (b) contacting each bait mixture with a nucleic acid sample to capture nucleic acid from the sample with the bait sets, wherein the second bait set in each mixture is provided at a concentration that is at or above a saturation point of the second bait set, wherein nucleic acid from the sample is captured by the bait sets; (c) sequencing a portion of the nucleic acids captured with each bait mixture to produce sets of sequence reads within an allocated number of sequence reads; (d) determining the read depth of sequence reads for the first bait set and the second bait set for each bait mixture; and (e) identifying at least one bait mixture that provides read depths for the second set of genomic regions; wherein the read depths for the second set of genomic regions provides a sensitivity of detecting of at least 0.0001%.

In some embodiments, the second bait set has a saturation point when subjected to titration, which titration comprises: generating a titration curve comprising: (i) measuring the capture efficiency of the second bait set as a function of the concentration of the baits; and (ii) identifying an inflection point within the titration curve, thereby identifying a saturation point associated with the second bait set.

In some embodiments, the saturation point is selected such that an observed capture efficiency increases by less than 20% at a concentration of the bait twice that of the first concentration. In some embodiments, the saturation point is selected such that an observed capture efficiency increases by less than 10% at a concentration of the bait twice that of the first concentration. In some embodiments, the saturation point is selected such that an observed capture efficiency increases by less than 5% at a concentration of the bait twice that of the first concentration. In some embodiments, the saturation point is selected such that an observed capture efficiency increases by less than 2% at a concentration of the bait twice that of the first concentration. In some embodiments, the saturation point is selected such that an observed capture efficiency increases by less than 1% at a concentration of the bait twice that of the first concentration.

In some embodiments, the first bait set or the second bait set selectively enrich for one or more nucleosome-associated regions of a genome, said nucleosome-associated regions comprising genomic regions having one or more genomic base positions with differential nucleosomal occupancy, wherein the differential nucleosomal occupancy is characteristic of a cell or tissue type of origin or disease state. In some embodiments, the first set of genomic regions or the second genomic regions comprises one or more actionable mutations, wherein the one or more actionable mutations comprise one or more of: (i) druggable mutations, (ii) mutations for therapeutic monitoring, (iii) disease specific mutations, (iv) tissue specific mutations, (v) cell type specific mutations, (vi) resistance mutations, and (vii) diagnostic mutations.

In some embodiments, the first and second genomic regions comprise at least a portion of each of at least 5 genes selected from Table 3. In some embodiments, the first and second genomic regions have a size between about 25 kilobases to 1,000 kilobases and a read depth of between 1,000 counts/base and 50,000 counts/base.

In one aspect, the present disclosure provides a method for enriching multiple genomic regions, comprising: (a) bringing a predetermined amount of nucleic acid from a sample in contact with a bait mixture comprising: (i) a first bait set that selectively hybridizes to a first set of genomic regions of the nucleic acid from the sample, which first bait set is provided at a first concentration that is less than a saturation point of the first bait set, and (ii) a second bait set that selectively hybridizes to a second set of genomic regions of the nucleic acid from the sample, which second bait set is provided at a second concentration that is at or above a saturation point of the second bait set; and (b) enriching the nucleic acid from the sample for the first set of genomic regions and the second set of genomic regions, thereby producing an enriched nucleic acid.

In some embodiments, the second bait set has a saturation point that is larger than substantially all of the saturation points associated with baits in the second bait set when a bait of the second bait set is subjected to a titration curve generated by (i) measuring capture efficiency of a bait of the second bait set as a function of the concentration of the bait, and (ii) identifying an inflection point within the titration curve, thereby identifying a saturation point associated with the bait. In some embodiments, the saturation point of the first bait set is selected such that an observed capture efficiency increases by less than 10% at a concentration of the bait twice that of the first concentration. In some embodiments, the first bait set or the second bait set selectively enrich for one or more nucleosome-associated regions of a genome, the nucleosome-associated regions comprising genomic regions having one or more genomic base positions with differential nucleosomal occupancy, wherein the differential nucleosomal occupancy is characteristic of a cell or tissue type of origin or disease state. In some embodiments, the method further comprises (c) sequencing the enriched nucleic acid to produce a plurality of sequence reads. In some embodiments, the method further comprises (d) producing an output comprising nucleic acid sequences representative of the nucleic acid from the sample.

In one aspect, the present disclosure provides a method comprising: (a) providing a plurality of bait mixtures, wherein each of the plurality of bait mixtures comprises a first bait set that selectively hybridizes to a first set of genomic regions and a second bait set that selectively hybridizes to a second set of genomic regions, wherein the first bait set is at different concentrations across the plurality of bait mixtures and the second bait set is at the same concentration across the plurality of bait mixtures; (b) contacting each of the plurality of bait mixtures with a nucleic acid sample to capture nucleic acids from the nucleic acid sample with the first bait set and the second bait set, wherein the second bait set in each bait mixture is provided at a first concentration that is at or above a saturation point of the second bait set, wherein nucleic acids from the nucleic acid sample are captured by the first bait set and the second bait set; (c) sequencing a portion of the nucleic acids captured with each bait mixture to produce sets of sequence reads within an allocated number of sequence reads; (d) determining the read depth of sequence reads for the first bait set and the second bait set for each bait mixture; and (e) identifying at least one bait mixture that provides read depths for the second set of genomic regions; wherein the read depths for the second set of genomic regions provides a sensitivity of detecting of a genetic variant of at least 0.0001% minor allele frequency (MAF). In some embodiments, steps (d) and/or (e) are optional.

In some embodiments, the second bait set has a saturation point when subjected to titration, which titration comprises generating a titration curve comprising: (i) measuring capture efficiency of the second bait set as a function of the concentration of the baits; and (ii) identifying an inflection point within the titration curve, thereby identifying a saturation point associated with the second bait set. In some embodiments, the saturation point is selected such that an observed capture efficiency increases by less than 10% at a concentration of the bait set twice that of the first concentration. In some embodiments, the first bait set or the second bait set selectively enrich for one or more nucleosome-associated regions of a genome, the nucleosome-associated regions comprising genomic regions having one or more genomic base positions with differential nucleosomal occupancy, wherein the differential nucleosomal occupancy is characteristic of a cell or tissue type of origin or disease state. In some embodiments, the first set of genomic regions comprises one or more actionable mutations, wherein the one or more actionable mutations comprise one or more of: (i) druggable mutations, (ii) mutations for therapeutic monitoring, (iii) disease specific mutations, (iv) tissue specific mutations, (v) cell type specific mutations, (vi) resistance mutations, and (vii) diagnostic mutations. In some embodiments, the first genomic regions comprise at least a portion of each of at least 5 genes selected from Table 1. In some embodiments, the first genomic regions have a size between about 25 kilobases to 1,000 kilobases and a read depth of between 1,000 counts/base and 50,000 counts/base. In some embodiments, the saturation point of the second bait set is selected such that an observed capture efficiency increases by less than 10% at a concentration of the bait twice that of the second concentration. In some embodiments, the second set of genomic regions comprises one or more actionable mutations, wherein the one or more actionable mutations comprise one or more of: (i) druggable mutations, (ii) mutations for therapeutic monitoring, (iii) disease specific mutations, (iv) tissue specific mutations, (v) cell type specific mutations, (vi) resistance mutations, and (vii) diagnostic mutations. In some embodiments, the second genomic regions comprise at least a portion of each of at least 5 genes selected from Table 1. In some embodiments, the second genomic regions have a size between about 25 kilobases to 1,000 kilobases and a read depth of between 1,000 counts/base and 50,000 counts/base.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings (also "Figure" and "FIG." herein), of which:

DETAILED DESCRIPTION

Figure 1:
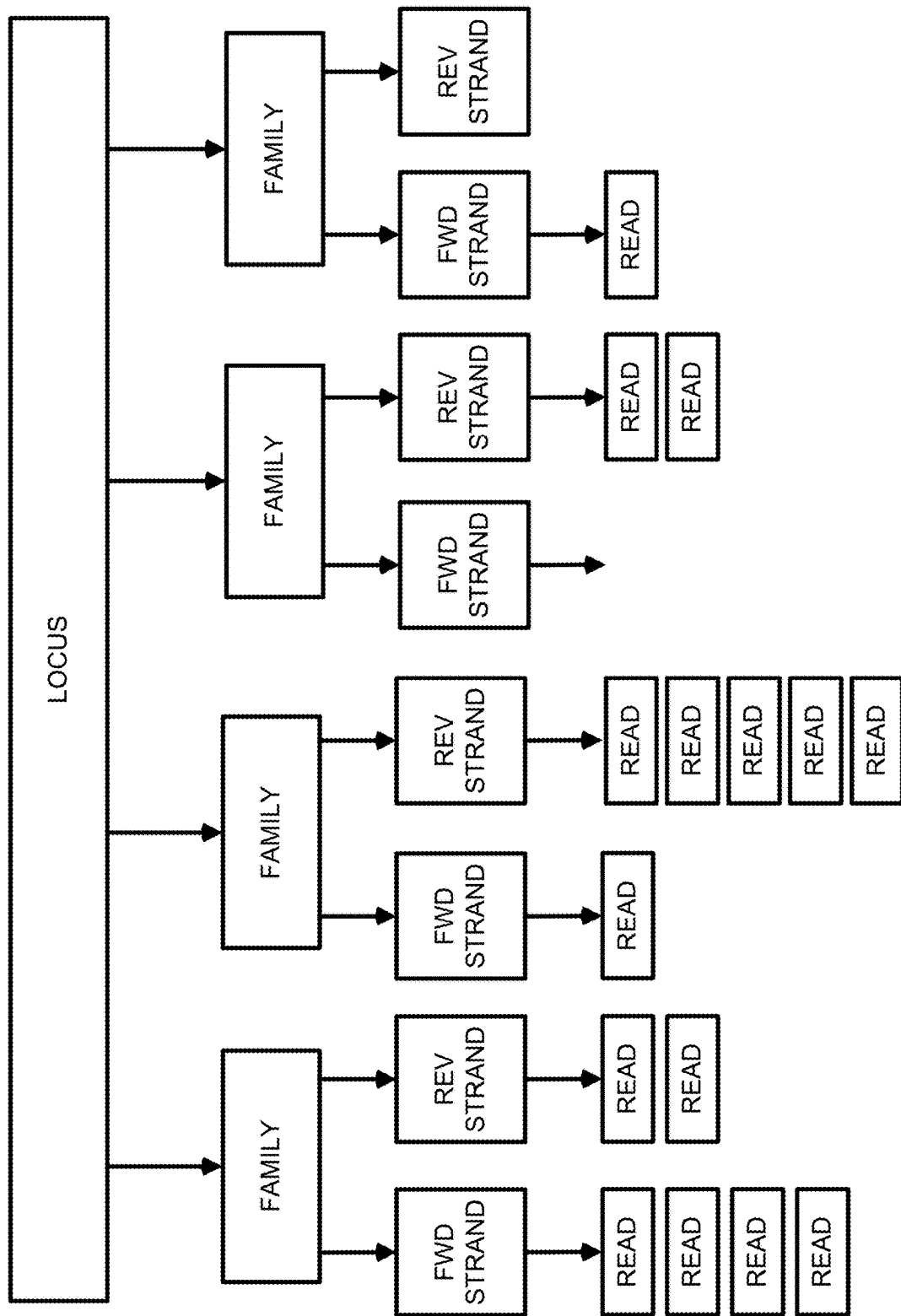
FIG. 1 illustrates how a plurality of reads may be generated for each locus enriched from a cell-free nucleic acid sample.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The term "genetic variant," as used herein, generally refers to an alteration, variant or polymorphism in a nucleic acid sample or genome of a subject. Such alteration, variant or polymorphism can be with respect to a reference genome, which may be a reference genome of the subject or other individual. Single nucleotide polymorphisms (SNPs) are a form of polymorphisms. In some examples, one or more polymorphisms comprise one or more single nucleotide variations (SNVs), insertions, deletions, repeats, small insertions, small deletions, small repeats, structural variant junctions, variable length tandem repeats, and/or flanking sequences. Copy number variations (CNVs), transversions and other rearrangements are also forms of genetic variation. A genomic alteration may be a base change, insertion, deletion, repeat, copy number variation, or transversion.

The term "polynucleotide," or "polynucleic acid" as used herein, generally refers to a molecule comprising one or more nucleic acid subunits (a "nucleic acid molecule"). A polynucleotide can include one or more subunits selected from adenosine (A), cytosine (C), guanine (G), thymine (T) and uracil (U), or variants thereof. A nucleotide can include A, C, G, T or U, or variants thereof. A nucleotide can include any subunit that can be incorporated into a growing nucleic acid strand. Such subunit can be an A, C, G, T, or U, or any other subunit that is specific to one or more complementary A, C, G, T or U, or complementary to a purine (i.e., A or G, or variant thereof) or a pyrimidine (i.e., C, T or U, or variant thereof). Identification of a subunit can enable individual nucleic acid bases or groups of bases (e.g., AA, TA, AT, GC, CG, CT, TC, GT, TG, AC, CA, or uracil-counterparts thereof) to be resolved. In some examples, a polynucleotide is deoxyribonucleic acid (DNA) or ribonucleic acid (RNA), or derivatives thereof. A polynucleotide can be single-stranded or double stranded.

A polynucleotide can comprise any type of nucleic acids, such as DNA and/or RNA. For example, if a polynucleotide is DNA, it can be genomic DNA, complementary DNA (cDNA), or any other deoxyribonucleic acid. A polynucleotide can be a cell-free nucleic acid. As used herein, the terms cell-free nucleic acid and extracellular nucleic acid can be used interchangeably. A polynucleotide can be cell-free DNA (cfDNA). For example, the polynucleotide can be circulating DNA. The circulating DNA can comprise circulating tumor DNA (ctDNA). The cell-free or extracellular nucleic acids can be derived from any bodily fluid including, but not limited to, whole blood, platelets, serum, plasma, synovial fluid, lymphatic fluid, ascites fluid, interstitial or extracellular fluid, the fluid in spaces between cells, gingival crevicular fluid, bone marrow, cerebrospinal fluid, saliva, mucous, sputum, semen, sweat, urine, cervical fluid or lavage, vaginal fluid or lavage, mammary gland or lavage, and/or any combination thereof. In some embodiments, the cell-free or extracellular nucleic acids can be derived from plasma. In some embodiments, a bodily fluid containing cells can be processed to remove the cells in order to purify and/or extract cell-free or extracellular nucleic acids. A polynucleotide can be double-stranded or single-stranded. Alternatively, a polynucleotide can comprise a combination of a double-stranded portion and a single-stranded portion.

Polynucleotides do not have to be cell-free. In some cases, the polynucleotides can be isolated from a sample. A sample can be a composition comprising an analyte. For example, a sample can be any biological sample isolated from a subject including, without limitation, bodily fluid, whole blood, platelets, serum, plasma, stool, red blood cells, white blood cells or leucocytes, endothelial cells, tissue biopsies, synovial fluid, lymphatic fluid, ascites fluid, interstitial or extracellular fluid, the fluid in spaces between cells, including gingival crevicular fluid, bone marrow, cerebrospinal fluid, saliva, mucous, sputum, semen, sweat, urine, or any other bodily fluids, and/or any combination thereof. A bodily fluid can include saliva, blood, or serum. For example, a polynucleotide can be cell-free DNA isolated from a bodily fluid, e.g., blood or serum. A sample can also be a tumor sample, which can be obtained from a subject by various approaches, including, but not limited to, venipuncture, excretion, ejaculation, massage, biopsy, needle aspirate, lavage, scraping, surgical incision, or intervention or other approaches. In some embodiments, a sample is a nucleic acid sample, e.g., a purified nucleic acid sample. In some embodiments, a nucleic acid sample comprises cell-free DNA (cfDNA). An analyte in a sample can be in various stages of purity. For example, a raw sample may be taken directly from a subject can contain the analyte in an unpurified state. A sample also may be enriched for an analyte. An analyte also may be present in the sample in isolated or substantially isolated form.

The polynucleotides can comprise sequences associated with cancer, such as acute lymphoblastic leukemia (ALL), acute myeloid leukemia (AML), adrenocortical carcinoma, Kaposi Sarcoma, anal cancer, basal cell carcinoma, bile duct cancer, bladder cancer, bone cancer, osteosarcoma, malignant fibrous histiocytoma, brain stem glioma, brain cancer, craniopharyngioma, ependymoblastoma, ependymoma, medulloblastoma, medulloeptithelioma, pineal parenchymal tumor, breast cancer, bronchial tumor, Burkitt lymphoma, Non-Hodgkin lymphoma, carcinoid tumor, cervical cancer, chordoma, chronic lymphocytic leukemia (CLL), chronic myelogenous leukemia (CML), colon cancer, colorectal cancer, cutaneous T-cell lymphoma, ductal carcinoma in situ, endometrial cancer, esophageal cancer, Ewing Sarcoma, eye cancer, intraocular melanoma, retinoblastoma, fibrous histiocytoma, gallbladder cancer, gastric cancer, glioma, hairy cell leukemia, head and neck cancer, heart cancer, hepatocellular (liver) cancer, Hodgkin lymphoma, hypopharyngeal cancer, kidney cancer, laryngeal cancer, lip cancer, oral cavity cancer, lung cancer, non-small cell carcinoma, small cell carcinoma, melanoma, mouth cancer, myelodysplastic syndromes, multiple myeloma, medulloblastoma, nasal cavity cancer, paranasal sinus cancer, neuroblastoma, nasopharyngeal cancer, oral cancer, oropharyngeal cancer, osteosarcoma, ovarian cancer, pancreatic cancer, papillomatosis, paraganglioma, parathyroid cancer, penile cancer, pharyngeal cancer, pituitary tumor, plasma cell neoplasm, prostate cancer, rectal cancer, renal cell cancer, rhabdomyosarcoma, salivary gland cancer, Sezary syndrome, skin cancer, nonmelanoma, small intestine cancer, soft tissue sarcoma, squamous cell carcinoma, testicular cancer, throat cancer, thymoma, thyroid cancer, urethral cancer, uterine cancer, uterine sarcoma, vaginal cancer, vulvar cancer, Waldenstrom macroglobulinemia, and/or Wilms Tumor.

A sample can comprise various amount of nucleic acid that contains genome equivalents. For example, a sample of about 30 ng DNA can contain about 10,000 ($10^4$) haploid human genome equivalents and, in the case of cfDNA, about 200 billion ($2 \times 10^{11}$) individual polynucleotide molecules. Similarly, a sample of about 100 ng of DNA can contain about 30,000 haploid human genome equivalents and, in the case of cfDNA, about 600 billion individual molecules.

A sample can comprise nucleic acids from different sources. For example, a sample can comprise germline DNA or somatic DNA. A sample can comprise nucleic acids carrying mutations. For example, a sample can comprise DNA carrying germline mutations and/or somatic mutations. A sample can also comprise DNA carrying cancer-associated mutations (e.g., cancer-associated somatic mutations).

The term "subject," as used herein, generally refers to an animal, such as a mammalian species (e.g., human) or avian (e.g., bird) species, or other organism, such as a plant. More specifically, the subject can be a vertebrate, a mammal, a mouse, a primate, a simian or a human. Animals include, but are not limited to, farm animals, sport animals, and pets. A subject can be a healthy individual, an individual that has or is suspected of having a disease or a pre-disposition to the disease, or an individual that is in need of therapy or suspected of needing therapy. A subject can be a patient.

The term "genome," as used herein, generally refers to an entirety of an organism's hereditary information. A genome can be encoded either in DNA or in RNA. A genome can comprise coding regions that code for proteins as well as non-coding regions. A genome can include the sequence of all chromosomes together in an organism. For example, the human genome has a total of 46 chromosomes. The sequence of all of these together may constitute a human genome. A genome may comprise a diploid or a haploid genome.

The term "bait," as used herein, generally refers to a target-specific oligonucleotide (e.g., a capture probe) designed and used to capture specific genomic regions of interest (e.g., targets, or predetermined genomic regions of interest). The bait may capture its intended targets by selectively hybridizing to complementary nucleic acids.

The term "bait panel" or "bait set panel," as used herein, generally refers to a set of baits targeted toward a selected set of genomic regions of interest. A bait panel or bait set panel may be referred to as a bait mixture. The bait panel may capture its intended targets in a single selective hybridization step.

The term "accuracy," of detecting a genetic variant (e.g., an indel), as used herein, generally refers to the percentage of candidate (e.g., detected) genetic variants detected through analysis of one or more sequence reads that are identified as a true genetic variant attributable to biological origin (e.g., not attributable to introduced error such as that stemming from sequencing or amplification error). The term "error rate," of detecting a genetic variant (e.g., an indel), as used herein, generally refers to the percentage of candidate (e.g., detected) genetic variants detected through analysis of one or more sequence reads that are identified as an introduced genetic variant attributable to non-biological origin (e.g., sequencing or amplification error). For example, if analysis of one or more sequence reads identifies 100 candidate genetic variants, of which 90 are attributable to biological origin and 10 are attributed to non-biological origin, then this analysis has an accuracy of detecting the genetic variant of 90% and an error rate of 10%.

The term "about" and its grammatical equivalents in relation to a reference numerical value can include a range of values up to plus or minus 10% from that value. For example, the amount "about 10" can include amounts from 9 to 11. In other embodiments, the term "about" in relation to a reference numerical value can include a range of values plus or minus 10%, 9%, 8%, 7%, 6%, 5%, 4%, 3%, 2%, or 1% from that value.

The term "at least" and its grammatical equivalents in relation to a reference numerical value can include the reference numerical value and greater than that value. For example, the amount "at least 10" can include the value 10 and any numerical value above 10, such as 11, 100, and 1,000.

The term "at most" and its grammatical equivalents in relation to a reference numerical value can include the reference numerical value and less than that value. For example, the amount "at most 10" can include the value 10 and any numerical value under 10, such as 9, 8, 5, 1, 0.5, and 0.1.

The terms "processing", "calculating", and "comparing" can be used interchangeably. The term can refer to determining a difference, e.g., a difference in number or sequence. For example, gene expression, copy number variation (CNV), indel, and/or single nucleotide variant (SNV) values or sequences can be processed.

The present disclosure provides methods and systems for multi-resolution analysis of cell-free nucleic acids (e.g., deoxyribonucleic acid (DNA)), wherein targeted genomic regions of interest may be enriched with capture probes ("baits") selected for one or more bait set panels using a differential tiling and capture scheme. A differential tiling and capture scheme uses bait sets of different relative concentrations to differentially tile (e.g., at different "resolutions") across genomic regions associated with baits, subject to a set of constraints (e.g., sequencer constraints such as sequencing load, utility of each bait, etc.), and capture them at a desired level for downstream sequencing. These targeted genomic regions of interest may include single-nucleotide variants (SNVs) and indels (i.e., insertions or deletions). The targeted genomic regions of interest may comprise backbone genomic regions of interest ("backbone regions") or hot-spot genomic regions of interest ("hot-spot regions" or "hotspot regions" or "hot-spots" or "hotspots"). While "hotpots" can refer to particular loci associated with sequence variants, "backbone" regions can refer to larger genomic regions, each of which can have one or more potential sequence variants. For example, a backbone region can be a region containing one or more cancer-associated mutations, while a hotspot can be a locus with a particular mutation associated with recurring cancer. Both backbone and hot-spot genomic regions of interest may comprise tumor-relevant marker genes commonly included in liquid biopsy assays (e.g., BRAF, BRCA, EGFR, KRAS, PIK3CA, ROS1, TP53, and others), for which one or more variants may be expected to be seen in subjects with cancer.

Among the set of tumor-relevant marker genes that may be selected for inclusion in a bait set panel, hot-spot genomic regions of interest may be selected to be represented by a higher proportion of sequence reads compared to the backbone genomic regions of interest in the experimental protocol. This experimental protocol may comprise steps including isolation, amplification, capture, sequencing, and data analysis. The selection of regions as hot-spot regions or backbone regions may be driven by considerations such as the capture efficiency, sequencing load, and/or utility associated with each of the regions and their corresponding bait. Utility may be assessed by the clinical relevance (e.g., "clinical value") of a genomic marker of interest (e.g., a tumor marker) toward a liquid biopsy assay, e.g., predetermined cancer driver mutations, genomic regions with prevalence across a relevant patient cohort, empirically identified cancer driver mutations, or nucleosome-associated genomic regions. For example, utility can be measured by a metric representative of expected yield of actionable and/or disease-associated genetic variants in detection or contribution toward determining tissue of origin or disease state of a sample. Utility may be a monotonically increasing function of clinical value.

Given that each sequencing run of a given sample of cell-free nucleic acids is typically limited by a certain total number of reads, a multi-resolution analysis approach to generate a bait set panel that preferentially enriches "hot-spot regions" as compared to backbone regions will enable efficient use of sequencing reads for genetic variant detection for cancer detection and assessment applications, by focusing sequencing at higher read depths for hot-spot regions over backbone regions. Using this approach may enable the improvement of a sample assay, given a limited or constrained sequencing load (e.g., number of sequenced reads per sample assayed), such that greater number of clinically actionable genetic variants may be detected per sample assay compared to an un-optimized sample assay.

The present disclosure provides methods for improving accuracy of detecting an insertion or deletion (indel) from a plurality of sequence reads derived from cell-free deoxyribonucleic acid (cfDNA) molecules in a bodily sample of a subject, which plurality of sequence reads are generated by nucleic acid sequencing. For each of the plurality of sequence reads associated with cfDNA molecules, a candidate indel may be identified. Each candidate indel may then be classified as either a true indel or an introduced indel, using a combination of predetermined expectations of (i) an indel being detected in one or more sequence reads of the plurality of sequence reads, (ii) that a detected indel is a true indel present in a given cfDNA molecule of the cell-free DNA molecules, given that an indel has been detected in the one or more of the sequence reads, and/or (iii) that a detected indel is introduced by non-biological error, given that an indel has been detected in the one or more of the sequence reads, in conjunction with one or more model parameters to perform a hypothesis test. This approach may reduce error and improve accuracy of detecting an indel from sequence read data.

Introduction

One embodiment of multi-resolution analysis proceeds as follows. Regions of a genome are selected for sequencing. These regions may be collectively referred to as a panel or a panel block. The panel is divided into a first set of genomic regions and a second set of genomic regions. The first set of genomic regions may be referred to as the backbone region, while the second set may be referred to as the hotspot regions. These regions may be divided between genes or within genes or outside genes as desired by the practitioner. For example, an exon of a gene may be divided into portions allocated to the hotspot region and portions allocated to the backbone region.

A first bait set and a second bait set are prepared which selectively hybridize to the first genomic regions and the second genomic regions, respectively. Using methods described herein, e.g., preparation of titration curves, bait set concentrations are determined which, for a test sample having a predetermined amount of DNA, capture DNA in the sample at a saturation point (for the bait set directed to the hotspot regions) and below the saturation point (for the bait set directed to the backbone regions). Capturing DNA molecules from a sample at the saturation point contributes to detecting genetic variants at the highest level of sensitivity because molecules genetic variants are more likely to be captured.

The amount of sequencing data that can be obtained from a sample is finite, and constrained by such factors as the quality of nucleic acid templates, number of target sequences, scarcity of specific sequences, limitations in sequencing techniques, and practical considerations such as time and expense. Thus, a "read budget" is a way to conceptualize the amount of genetic information that can be extracted from a sample. A per-sample read budget can be selected that identifies the total number of base reads to be allocated to a test sample comprising a predetermined amount of DNA in a sequencing experiment. The read budget can be based on total reads produced, e.g., including redundant reads produced through amplification. Alternatively, it can be based on number of unique molecules detected in the sample. In certain embodiments read budget can reflect the amount of double-stranded support for a call at a locus. That is, the percentage of loci for which reads from both strands of a DNA molecule are detected.

Factors of a read budget include read depth and panel length. For example, a read budget of 3,000,000,000 reads can be allocated as 150,000 bases at an average read depth of 20,000 reads/base. Read depth can refer to number of molecules producing a read at a locus. In the present disclosure, the reads at each base can be allocated between bases in the backbone region of the panel, at a first average read depth and bases in the hotspot region of the panel, at a deeper read depth.

By way of non-limiting example, if a read budget consists of 100,000 read counts for a given sample, those 100,000 read counts will be divided between reads of backbone regions and reads of hotspot regions. Allocating a large number of those reads (e.g., 90,000 reads) to backbone regions will result in a small number of reads (e.g., the remaining 10,000 reads) being allocated to hotspot regions. Conversely, allocating a large number of reads (e.g., 90,000 reads) to hotspot regions will result in a small number of reads (e.g., the remaining 10,000 reads) being allocated to backbone regions. Thus, a skilled worker can allocate a read budget to provide desired levels of sensitivity and specificity. In certain embodiments, the read budget can be between 100,000,000 reads and 100,000,000,000 reads, e.g., between 500,000,000 reads and 50,000,000,000 reads, or between 1,000,000,000 reads and 5,000,000,000 reads across, for example, 20,000 bases to 100,000 bases.

First and second sensitivity levels are selected for detection of genetic variants in the backbone and hotspot regions, respectively. Sensitivity, as used herein, refers to the detection limit of a genetic variant as a function of frequency in a sample. For example, the sensitivity may be at least 1%, at least 0.1%, at least 0.01%, at least 0.001%, at least 0.0001%, or at least 0.00001%, meaning that a given sequence can be detected in a sample at a frequency of at least 10%, at least 0.10%, at least 0.010%, at least 0.001%, at least 0.00010%, or at least 0.00001%, respectively. That is, genetic variants present in the sample at the levels are detectable by sequencing. Typically, sensitivity selected for hotspot regions will be higher than sensitivity selected for backbone regions. For example, the sensitivity level for hotspot regions may be selected at at least 0.001%, while the sensitivity level for background regions may be selected at at least 0.1% or at least 1%.

The relative concentrations of bait sets directed to background regions and hotspot regions can be selected to optimize reads in a sequencing experiment with respect to selected read budget and selected sensitivities for the backbone and hotspot regions for a selected sample. So, for example, given a test sample containing a predetermined amount of DNA, and a hotspot bait set that captures DNA for the hotspot regions at saturation, an amount of backbone bait set that is below saturation for the sample is selected such that in a sequencing experiment producing reads within the selected read budget, the resultant read set detects genetic variants in the hotspot regions and in the backbone regions at the preselected sensitivity levels.

The relative amounts of the bait sets is a function of several factors. One of these factors is the relative proportion of the panel allocated to the hotspot regions and to the backbone regions respectively. The larger the relative percentage of hotspot regions in the panel, the fewer the number of reads and the budget that can be allocated to the backbone region. Another factor is the selected sensitivity of detection for hotspot regions. For a given sample, the higher the sensitivity that is necessary for the hotspot regions, the lower sensitivity will be for the backbone region. Another factor is the read budget. For a sensitivity for the hotspot regions, the smaller the read budget, the lower the sensitivity possible for the backbone region. Another factor is the size of the overall panel. For any given read budget, the larger the panel, the more sensitivity of the backbone regions must be sacrificed to achieving desired sensitivity at the hotspot regions.

It will be evident that for any given read budget, increasing the percentage of reads allocated to the backbone regions will decrease the sensitivity of detection at the hotspot regions. Conversely, increasing the sensitivity of detection at the hotspot regions, by increasing the amount of the read budget allocated to hotspot regions, decreases the detection of the backbone regions. Accordingly, the relative sensitivity levels of hotspot regions can be high enough to achieve targeted detection levels, while sensitivity level at backbone regions are not so low such that meaningful levels of genetic variants are missed. These relative levels are selected by the practitioner to achieve the desired results. In some embodiments, the skilled worker will use a bait mixture calculated to capture all (or substantially all) hotspot regions in a sample and a portion of the backbone regions, such that the read depth of the captured regions will provide desired hotspot and backbone sensitivities.

Nucleosome-Associated Genomic Regions

In an aspect, a bait set panel may comprise one or more bait sets that selectively enrich for one or more nucleosome-associated regions of a genome. Nucleosome-associated regions may comprise genomic regions having one or more genomic base positions with differential nucleosomal occupancy. Differential nucleosomal occupancy may be characteristic of a cell or tissue type of origin or disease state. Analysis of differential nucleosomal occupancy may be performed using one or more nucleosomal occupancy profiles of a given cell or tissue type. Examples of nucleosomal occupancy profiling techniques include Statham et al., Genomics Data, Volume 3, March 2015, Pages 94-96 (2015), which is entirely incorporated herein by reference. Cell-free nucleic acids in a sample obtained from a subject may be primarily shed through a combination of apoptotic and necrotic processes in cells, tissues, and organs. As a result of variable nucleosomal occupancy and protection against DNA cleavage in certain locations of a genome, nucleosomal patterns or profiles associated with apoptotic processes and necrotic processes may be evident from analyzing cell-free nucleic acid fragments for nucleosome-associated regions of a genome.

Detection of such nucleosome-associated patterns can be used, independently or in conjunction with detected somatic variants, to monitor a condition in a subject. For example, as a tumor expands, the ratio of necrosis to apoptosis in the tumor micro-environment may change. Such changes in necrosis and/or apoptosis can be detected by selectively enriching a cell-free nucleic acid sample for one or more nucleosome-associated regions. As another example, a distribution of fragment lengths may be observed due to differential nucleosomal protection across different cell types, or across tumor vs. non-tumor cells. Analysis of nucleosome-associated regions for fragment length distribution may be clinically relevant for cancer detection and assessment applications. This analysis may comprise selectively enriching for nucleosome-associated regions, then sequencing the enriched regions to produce a plurality of sequence reads representative of the nucleic acid sample, and analyzing the sequence reads for genetic variants and nucleosome profiles of interest.

Once nucleosome-associated regions have been identified, they may be used for modular panel design. See below. Such modular panel design may allow for designs of a set of probes or baits that selectively enrich regions of the genome that are relevant for nucleosomal profiling. By incorporating this "nucleosomal awareness," sequence data from many individuals can be gleaned to optimize the procedure of panel design, e.g., the determination of which genomic locations to target and the optimal concentration of probes for these genomic locations.

By incorporating knowledge of both somatic variations and structural variations and instability, panels of probes, baits or primers can be designed to target specific portions of the genome ("hotspots") with known patterns or clusters of structural variation or instability. For example, statistical analysis of sequence data reveals a series of accumulated somatic events and structural variations, and thereby enables clonal evolution studies. The data analysis reveals important biological insights, including differential coverage across cohorts, patterns indicating the presence of certain subsets of tumors, foreign structural events in samples with high somatic mutation load, and differential coverage attributed from blood cells versus tumor cells.

A localized genomic region refers to a short region of the genome that may range in length from, or from about, 2 to 200 base pairs, from 2 to 190 base pairs, from 2 to 180 base pairs, from 2 to 170 base pairs, from 2 to 160 base pairs, from 2 to 150 base pairs, from 2 to 140 base pairs, from 2 to 130 base pairs, from 2 to 120 base pairs, from 2 to 110 base pairs, from 2 to 100 base pairs, from 2 to 90 base pairs, from 2 to 80 base pairs, from 2 to 70 base pairs, from 2 to 60 base pairs, from 2 to 50 base pairs, from 2 to 40 base pairs, from 2 to 30 base pairs, from 2 to 20 base pairs, from 2 to 10 base pairs, and/or from 2 to 5 base pairs. Each localized genomic region may contain a pattern or cluster of significant structural variation or instability. Genome partitioning maps may be provided to identify relevant localized genomic regions. A localized genomic region may contain a pattern or cluster of significant structural variation or structural instability. A cluster may be a hotspot region within a localized genomic region. The hotspot region may contain one or more significant fluctuations or peaks. A structural variation may be selected from the group consisting of: an insertion, a deletion, a translocation, a gene re-arrangement, methylation status, a micro-satellite, a copy number variation, a copy number-related structural variation, or any other variation which indicates differentiation. A structural variation can cause a variation in nucleosomal positioning.

A genome partitioning map may be obtained by: (a) providing samples of cell-free DNA or RNA from two or more subjects in a cohort, (b) obtaining a plurality of sequence reads from each of the samples of cell-free DNA or RNA, and (c) analyzing the plurality of sequence reads to identify one or more localized genomic regions, each of which contains a pattern or cluster of significant structural variation or instability. Statistical analysis may be performed on sequence information to associate a set of sequence reads with one or more nucleosomal occupancy profiles representing distinct cohorts (e.g., a group of subjects with a common characteristic such as a disease state or a non-disease state).

The statistical analysis may comprise providing one or more genome partitioning maps listing relevant genomic intervals representative of genes of interest for further analysis. The statistical analysis may further comprise selecting a set of one or more localized genomic regions based on the genome partitioning maps. The statistical analysis may further comprise analyzing one or more localized genomic regions in the set to obtain a set of one or more nucleosomal map disruptions. The statistical analysis may comprise one or more of (e.g., one or more, two or more, or three of): pattern recognition, deep learning, and unsupervised learning.

A nucleosomal map disruption is a measured value that characterizes a given localized genomic region in terms of biologically relevant information. A nucleosomal map disruption may be associated with a driver mutation chosen from the group consisting of: wild-type, somatic variant, germline variant, and DNA methylation.

One or more nucleosomal map disruptions may be used to classify a set of sequence reads as being associated with one or more nucleosomal occupancy profiles representing distinct cohorts. These nucleosomal occupancy profiles may be associated with one or more assessments. An assessment may be considered as part of a therapeutic intervention (e.g., treatment options, selection of treatment, further assessment by biopsy and/or imaging).

An assessment may be selected from the group consisting of: indication, tumor type, tumor severity, tumor aggressiveness, tumor resistance to treatment, and tumor clonality. An assessment of tumor clonality may be determined from observing heterogeneity in nucleosomal map disruption across cell-free DNA molecules in a sample. An assessment of relative contributions of each of two or more clones is determined.

Each of the one or more nucleosome-associated regions of a bait set panel may comprise at least one of: (i) significant structural variation, comprising a variation in nucleosomal positioning, said structural variation selected from the group consisting of: an insertion, a deletion, a translocation, a gene rearrangement, methylation status, a micro-satellite, a copy number variation, a copy number-related structural variation, or any other variation which indicates differentiation; and (ii) instability, comprising one or more significant fluctuations or peaks in a genome partitioning map indicating one or more locations of nucleosomal map disruptions in a genome. The one or more bait sets of a bait set panel may be configured to capture nucleosome-associated regions of the genome based on a function of a plurality of reference nucleosomal occupancy profiles associated with one or more disease states and one or more non-disease states.

The one or more bait sets of a bait set panel may selectively enrich for one or more nucleosome-associated regions in a cell-free deoxyribonucleic acid (cfDNA) sample. For example, the bait set may selectively enrich for one or more nucleosome-associated regions by bringing a nucleic sample in contact with the bait set, and allowing the bait set to selectively hybridize to the set of nucleosome-associated genomic regions associated with the bait set.

In an aspect, a method for enriching a nucleic acid sample for nucleosome-associated regions of a genome may comprise (a) bringing a nucleic acid sample in contact with a bait set panel, said bait set panel comprising one or more bait sets that selectively enrich for one or more nucleosome-associated regions of a genome; and (b) enriching the nucleic acid sample for one or more nucleosome-associated regions of a genome. The one or more bait sets in a bait set panel may be configured to capture nucleosome-associated regions of the genome based on a function of a plurality of reference nucleosomal occupancy profiles associated with one or more disease states and one or more non-disease states. The plurality of reference nucleosomal occupancy profiles may serve as a "map" for which analysis may reveal patterns or clusters of genomic regions and/or locations which may be targeted for capture for nucleosome-associated variant detection.

The one or more bait sets in a bait set panel may selectively enrich for the one or more nucleosome-associated regions in a cell-free deoxyribonucleic acid (cfDNA) sample. The method for enriching a nucleic acid sample for nucleosome-associated regions of a genome may further comprise sequencing the enriched nucleic acids to produce sequence reads of the nucleosome-associated regions of a genome. These sequence reads may be aligned to a reference genome and analyzed for nucleosome-associated and/or genetic variants (e.g., SNVs and/or indels).

In an aspect, a method for generating a bait set may comprise (a) identifying one or more regions of a genome, said regions associated with a nucleosome profile, and (b) selecting a bait set to selectively capture said regions. A bait set in a bait set panel may selectively enrich for one or more nucleosome-associated genomic regions in a cell-free deoxyribonucleic acid (cfDNA) sample. For example, the bait set may selectively enrich for one or more nucleosome-associated regions by bringing a nucleic sample in contact with the bait set, and allowing the bait set to selectively hybridize to the set of nucleosome-associated genomic regions associated with the bait set.

Bait Panels for Enrichment of Multiple Genomic Regions

In an aspect, a bait panel may comprise a first bait set that selectively hybridizes to a first set of genomic regions of a nucleic acid sample comprising a predetermined amount of DNA, wherein the first bait set may be provided at a first concentration ratio that is less than a saturation point of the first bait set; and a second bait set that selectively hybridizes to a second set of genomic regions of the nucleic acid sample, wherein the second bait set may be provided at a second concentration ratio that is associated with a saturation point of the second bait set. As used herein, a concentration associated with a saturation point can be at or above the saturation point. In some embodiments, a concentration associated with a saturation point is at or above a point that is 10% below the saturation point. The first set of genomic regions may comprise one or more backbone genomic regions. The second set of genomic regions may comprise one or more hotspot genomic regions. The predetermined amount of DNA may be about 200 ng, about 150 ng, about 125 ng, about 100 ng, about 75 ng, about 50 ng, about 25 ng, about 10 ng, about 5 ng, and/or about 1 ng.

In an aspect, a method for enriching for multiple genomic regions may comprise bringing a predetermined amount of a nucleic acid sample in contact with a bait panel comprising (i) a first bait set that selectively hybridizes to a first set of genomic regions of the nucleic acid sample, which may be provided at a first concentration ratio that is less than a saturation point of the first bait set, and (ii) a second bait set that selectively hybridizes to a second set of genomic regions of the nucleic acid sample, which may be provided at a second concentration ratio that is associated with a saturation point of the second bait set; and enriching the nucleic acid sample for the first set of genomic regions and the second set of genomic regions.

Enriching can comprise the following steps: (a) bringing sample nucleic acid into contact with a bait set; (b) capturing nucleic acids from the sample by hybridizing them to probes in the bait set; and (c) separating captured nucleic acids from un-captured nucleic acids.

Using this approach, capture of the second set of genomic regions at a saturation point of its bait set may yield high-sensitivity detection of variants of the second set of genomic regions (e.g., hot-spot regions), while capture of the first set of genomic regions below the saturation point of its bait set may be desired for the first set of genomic regions (e.g., backbone regions). The flexibility of this method to adjust the capture of different bait sets at or below their saturation levels may be leveraged to strategically select genomic regions of interest for hot-spot or backbone bait set panels, given each genomic region's characteristics such as sequencing load and utility.

The method may further comprise sequencing the enriched nucleic acids to produce a plurality of sequence reads of the first set of genomic regions and the second set of genomic regions. These sequence reads may be analyzed for cancer-relevant genetic variants (e.g., SNVs and indels) for cancer detection and assessment applications.

The skilled worker will appreciate that saturation point refers to saturation of binding kinetics. In essence, as the concentration of a bait (or set of baits) increases, the amount of target that binds to the bait (or set of baits) will also increase. However, the amount of target in a given sample will be fixed, and thus, at a certain point, effectively all the target in the sample will be bound to the bait (or set of baits). Therefore, as bait concentrations increase beyond this point, the amount of bound target will not substantially increase because the system will approach binding equilibrium (the rates at which bait molecules bind and release target molecules will start to converge).

Saturation point refers to a concentration or amount of bait at which point increasing that concentration or amount does not substantially increase the amount of target material captured from a sample, e.g., that point at which increases in the concentration of bait produce increasingly diminished increases in total amount of target material captured. In some embodiments, the point at which increasing the concentration or amount of a bait does not substantially increase the amount of target material captured from a sample is the point at which increasing the concentration or amount of bait produces no increase in the amount of target captured from the sample. The saturation point can be an inflection point on a saturation curve measuring the amount of captured target nucleic acid with increasing concentrations of the bait set. For example, the saturation point can be the point at which an increase of 100% in the bait concentration (e.g., 2× or twice the concentration) increases an amount of target captured by any of less than 20%, less than 19%, less than 18%, less than 17%, less than 16%, less than 15%, less than 14%, less than 13%, less than 12%, less than 110, less than 10%, less than 9%, less than 8%, less than 7%, less than 6%, less than 5%, less than 4%, less than 3%, less than 2%, or less than 1%. In some embodiments, an increase of 50% in the bait concentration (e.g., 1.5× or one-and-a-half times the concentration) increases an amount of target captured by any of less than 20%, less than 19%, less than 18%, less than 17%, less than 16%, less than 15%, less than 14%, less than 13%, less than 12%, less than 11%, less than 10%, less than 9%, less than 8%, less than 7%, less than 6%, less than 5%, less than 4%, less than 3%, less than 2%, or less than 1%. In some embodiments, an increase of 20% in the bait concentration (e.g., 1.2×) increases an amount of target captured by any of less than 20%, less than 19%, less than 18%, less than 17%, less than 16%, less than 15%, less than 14%, less than 13%, less than 12%, less than 11%, less than 10%, less than 9%, less than 8%, less than 7%, less than 6%, less than 5%, less than 4%, less than 3%, less than 2%, or less than 1%. In some embodiments, an increase of 10% in the bait concentration (e.g., 1.1×) increases an amount of target captured by any of less than 20%, less than 19%, less than 18%, less than 17%, less than 16%, less than 15%, less than 14%, less than 13%, less than 12%, less than 11%, less than 10%, less than 9%, less than 8%, less than 7%, less than 6%, less than 5%, less than 4%, less than 3%, less than 2%, or less than 1%.

As another example, the saturation point can be the point at which an increase of 100% in the bait concentration (e.g., 2× or twice the concentration) increases an amount of target captured by at most 20%. The saturation point can be the point at which an increase of 50% in the bait concentration (e.g., 1.5× or twice the concentration) increases an amount of target captured by at most 20%. The saturation point can be the point at which an increase of 20% in the bait concentration (e.g., 1.2× or twice the concentration) increases an amount of target captured by at most 20%. The saturation point can be the point at which an increase of 10% in the bait concentration (e.g., 1.1× or twice the concentration) increases an amount of target captured by at most 20%.

A saturation curve can be generated, for example, by titrating differing amounts of target nucleic acids against a fixed or varying amount of baits (e.g., baits fixed on a microarray) to measure the amount of target nucleic acid (including, for example, the number of unique molecules) bound to the baits. A saturation curve also can be generated, for example, by titrating differing amounts of baits against a fixed or varying amount of target nucleic acids to measure the amount of target nucleic acid (including, for example, the number of unique molecules) bound to the baits. In some embodiments, a saturation curve can be generated using a subset of sequence reads as a measure of target nucleic acid (e.g., unique molecule count) captured. For example, sequence reads can be categorized as having either single stranded support (when all reads within a group of unique reads are from the same original nucleic acid strand of a double stranded nucleic acid such as DNA) or double stranded support (when the reads within a group of unique reads are from both original nucleic acid strands of a double stranded nucleic acid such as DNA). In embodiments selecting for double stranded support, the skilled worker would understand to count only captured unique molecules for which both strands are observed. Double stranded support can be determined, for example, by differentially tagging each of the two different strands of a nucleic acid such that the reads for each strand can be counted separately. In some embodiments, a target nucleic acid with double stranded support will require a higher amount of bait to reach saturation for that target than would be required for a bait with single stranded support.

Figure 6:
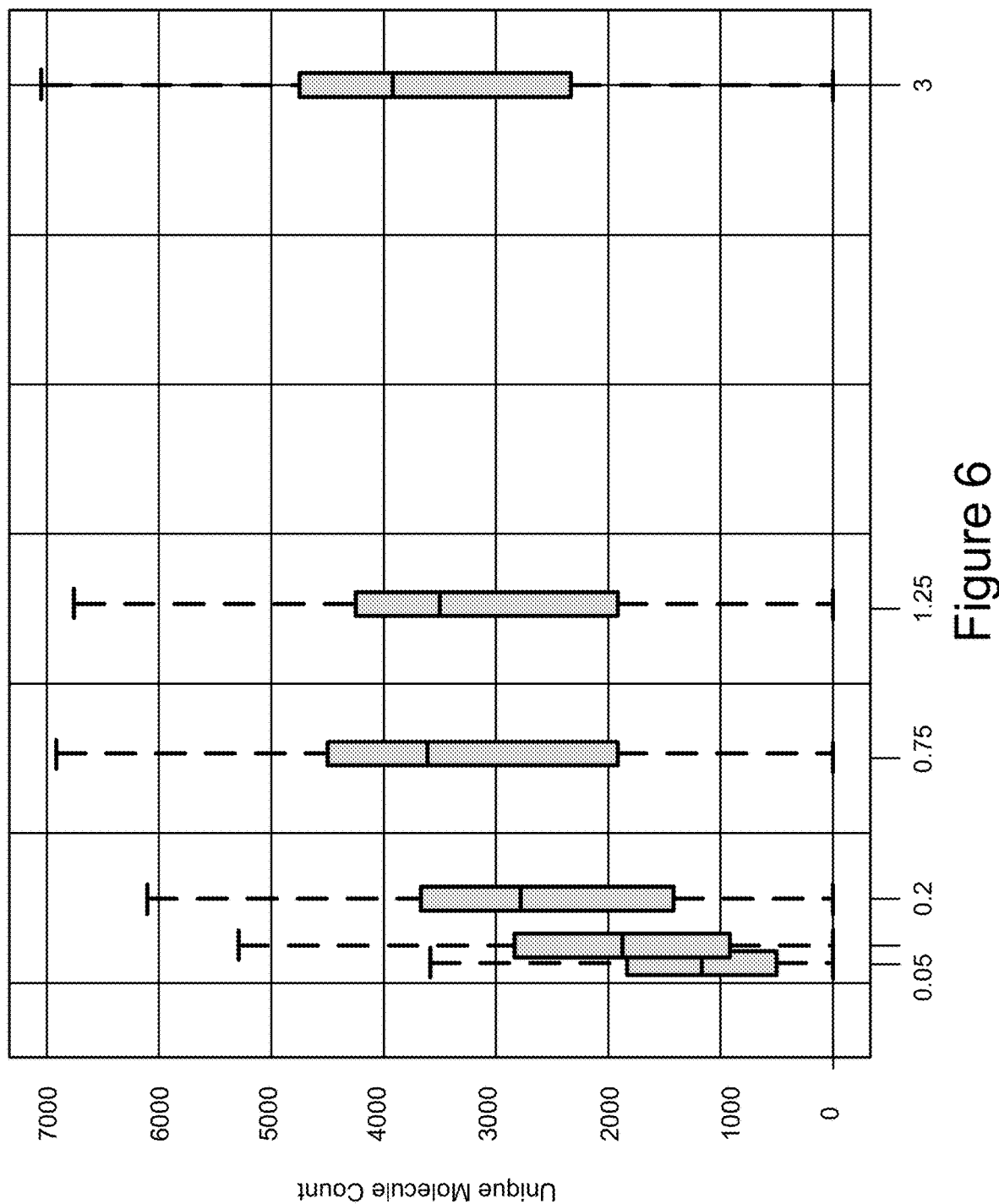
FIG. 6 illustrates an exemplary saturation curve showing unique molecule count on the y-axis as a function of input cfDNA amount on the x-axis.

FIG. 6 depicts an exemplary saturation curve showing unique molecule count on the y-axis as a function of input bait amount on the x-axis. At each input amount (shown as a series of volumes of a bait solution), the amount of bait panel was titrated to generate the curve. Exemplary experimental titration curve designs are shown in Table 1 and Table 2 below. Number of unique sequence reads vs. input bait amount can be used to generate a titration curve as shown in FIG. 6.

TABLE 1

Titration curve design

| Amount of bait (backbone or hotspot; μl) | Input target amount (0, 5, 15 or 30 ng) | | | | | | | |
|---|---|---|---|---|---|---|---|---|
| | Vol. A | Vol. B | Vol. C | Vol. D | Vol. E | Vol. F | Vol. G | Vol. H |
| Backbone 1 (ng of input target nucleic acid) | 0 | 5 | 5 | 0 | 5 | 0 | 5 | 5 |
| Backbone 2 (ng of input target nucleic acid) | 30 | 30 | 30 | 0 | 30 | 0 | 30 | 30 |
| Hotspot 1 (ng of input target nucleic acid) | 0 | 0 | 0 | 0 | 0 | 5 | 0 | 0 |
| Hotspot 2 (ng of input target nucleic acid) | 0 | 0 | 0 | 0 | 0 | 15 | 0 | 0 |
| Hotspot 3 (ng of input target nucleic acid) | 0 | 0 | 0 | 0 | 0 | 30 | 0 | 0 |
| Backbone 3 (ng of input target nucleic acid) | 5 | 5 | 5 | 0 | 5 | 0 | 5 | 5 |
| Backbone 4 (ng of input target nucleic acid) | 0 | 0 | 15 | 0 | 15 | 0 | 15 | 15 |
| Backbone 5 (ng of input target nucleic acid) | 30 | 30 | 30 | 0 | 30 | 0 | 30 | 30 |
| Hotspot 4 (ng of input target nucleic acid) | 5 | 5 | 0 | 5 | 0 | 5 | 0 | 0 |
| Hotspot 5 (ng of input target nucleic acid) | 0 | 0 | 0 | 0 | 0 | 15 | 0 | 0 |
| Hotspot 6 (ng of input target nucleic acid) | 30 | 30 | 0 | 30 | 0 | 30 | 0 | 0 |

TABLE 2

Titration curve design. Hybridization performed at 65° C.

| Condition # | Hotspot bait (μl) | Backbone bait (μl) | Input target nucleic acid amount (ng) |
|---|---|---|---|
| 1 | A | B | 5 |
| 2 | A | B | 5 |
| 3 | A | B | 5 |
| 4 | A | B | 5 |
| 5 | A2 | B1 | 5 |
| 6 | A2 | B1 | 5 |
| 7 | A2 | B2 | 5 |
| 8 | A2 | B2 | 5 |
| 9 | A | B1 | 15 |
| 10 | A | B1 | 15 |
| 11 | A | B2 | 15 |
| 12 | A | B2 | 15 |
| 13 | A2 | B1 | 15 |
| 14 | A2 | B1 | 15 |
| 15 | A2 | B2 | 15 |
| 16 | A2 | B2 | 15 |
| 17 | A2 | B2 | 30 |
| 18 | A2 | B2 | 30 |

Using a titration curve such as that of FIG. 6, a person of skill in the art can calculate a saturation point. For example, looking at Vol. 0.8×, the unique molecule count is approximately 2700. At 2× the amount of bait (Vol. 1.6×), the unique molecule count is approximately 3200, a difference of 500. Thus, doubling the amount of bait results in an increase in capture of about 18.5%. By contrast, at Vol. 2×, the unique molecule count is approximately 3250, and at 1 μl, the unique molecule count is approximately 3500, a difference of 250. Doubling the amount of bait here results in an increase in capture of only about 7.7%. Accordingly, a person of skill in the art looking to use a saturation point at which an increase of 100% in the bait concentration to increase an amount of target captured by less than 8% might therefore use Vol. 2× of bait as the saturation point.

At the saturation point, the bait set can capture any of at least 40%, at least 50%, at least 60%, at least 70%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, and/or at least 99% of a target sequence in a sample. Saturation point can refer to the saturation point of a bait set or of a particular bait, depending on the context in which the term is used.

The saturation point of a bait set may be determined by the following method: (a) for each of the baits in the bait set, generating a titration curve comprising (i) measuring the capture efficiency of the bait on a given amount of input sample (e.g., test sample) as a function of the concentration of the bait, and (ii) identifying an inflection point within the titration curve, thereby identifying a saturation point associated with the bait; and (b) selecting a saturation point that is larger than substantially all of the saturation points associated with baits in the bait set, thereby determining the saturation point of the bait set. The selection of a saturation point may be influenced by capture efficiency of a bait and the associated costs, such that the concentration at the saturation point may be high enough to achieve a desired capture efficiency, while still low enough to ensure reasonable assay reagent costs.

The capture efficiency of a bait may be determined by (a) providing a plurality of nucleic acid samples obtained from a plurality of subjects in a cohort; (b) hybridizing the bait with each of the nucleic acid samples, at each of a plurality of concentrations of the bait; (c) enriching with the bait, a plurality of genomic regions of the nucleic acid samples, at each of the plurality of concentrations of the bait; and (d) measuring number of unique nucleic acid molecules or nucleic acid molecules with representation of both strands of an original double-stranded nucleic acid molecule representing the capture efficiency at each of the plurality of concentrations of the bait. Typically, the capture efficiency of a bait (e.g., the percentage of molecules containing the target genomic region of the bait that are captured from a sample comprising such molecules) increases rapidly with concentration until an inflection point is reached, after which the percentage of captured molecules increases much more slowly.

An inflection point may be a first concentration of a bait such that observed capture efficiency does not increase significantly at concentrations of the bait greater than the first concentration. An inflection point may be a first concentration of the bait such that an observed increase between (1) the capture efficiency at a bait concentration of twice the first concentration compared to (2) the capture efficiency at the first bait concentration, is less than about 1%, less than about 2%, less than about 3%, less than about 4%, less than about 5%, less than about 6%, less than about 7%, less than about 8%, less than about 9%, less than about 10%, less than about 12%, less than about 14%, less than about 16%, less than about 18%, less than about 20%, less than about 30%, less than about 40%, or less than about 50%. Such an identified inflection point can be considered a saturation point associated with a bait. A bait can be used at a concentration of a saturation point in an assay to enable optimal capture of a target genomic region and hence sensitivity of detecting genetic variants of the target genomic region. In some embodiments, the saturation point associated with a bait set is the saturation point of the weakest bait in that bait set. For example, the bait set has a saturation point that is larger than substantially all of the saturation points associated with baits in the bait set when a bait of the bait set is subjected to a titration curve generated by (i) measuring the capture efficiency of a bait of the bait set as a function of the concentration of the bait, and (ii) identifying an inflection point within the titration curve, thereby identifying a saturation point associated with the bait. When each bait in the bait set is at a first concentration that is least at its saturation point, the bait set will have captured target sequences such that observed capture efficiency of the target sequences increases by less than 20% at a concentration of the baits twice that of the first concentration The nucleic acid sample may be a cell-free nucleic acid sample (e.g., cfDNA). A method for enriching for multiple genomic regions may further comprise sequencing the enriched nucleic acid sample to produce a plurality of sequence reads. A method for enriching for multiple genomic regions may further comprise producing an output comprising a nucleic acid sequence representative of the nucleic acid sample. This nucleic acid sequence may then be aligned to a reference genome and analyzed for cancer-relevant genetic variants through bioinformatics approaches.

An original molecule can produce redundant sequence reads, for example, after amplification and sequencing of amplicons, or by repeated sequencing of the same molecule. Redundant sequence reads from an original molecule can be collapsed into a consensus sequence (e.g., a "unique sequence") representing the sequence of the original molecule. This can be done by generating a consensus sequence for the full molecule, for part of the molecule or at a single nucleotide position in the molecule (consensus nucleotide). As used herein "sequenced polynucleotide" refers either to sequence reads generated from amplicons of an original molecule, or a consensus sequence of an original molecule derived from such amplicons. Unique reads are reads that are different from every other read. Reads can be unique based on the sequence of an original molecule, or based on the sequence of an original molecule plus one or more barcode sequences attached to an original molecule. For example, two identical original molecules can still yield unique reads if their barcodes are different. Likewise, two different original molecules will produce unique reads even if their barcodes are the same. Consensus sequences can be unique sequences when they are generated by grouping unique reads.

In an aspect, a bait panel may comprise a first set that selectively captures backbone regions of a genome, said backbone regions associated with a ranking function of sequencing load and utility, wherein the ranking function of each backbone region has a value less than a predetermined threshold value; and a second bait set that selectively captures hotspot regions of a genome, said hotspot regions associated with a ranking function of sequencing load and utility, wherein the ranking function of each hotspot region has a value greater than or equal to the predetermined threshold value. This approach may use at least two bait sets corresponding to backbone and hotspot regions.

Hotspot regions may be relatively more important than backbone regions to capture and analyze in a given cell-free nucleic acid sample due to their relatively high utility and/or relatively low sequencing load. The selection of a given region as a hotspot region or a backbone region depends on its ranking function value, which is calculated as a function of sequencing load and utility. A ranking function value may be calculated as utility of a genomic region divided by sequencing load of a genomic region.

The backbone or hotspot regions may comprise one or more nucleosome informative regions. Nucleosome informative regions may comprise a region of maximum nucleosome differentiation. The bait panel may further comprise a second bait set that selectively captures disease informative regions. The baits in the first bait set may be at a first concentration (e.g., a first concentration relative to the bait panel), and the baits in the second bait set may be at a second concentration (e.g., a second concentration relative to the bait panel).

In an aspect, a method for generating a bait set may comprise identifying one or more backbone genomic regions of interest, wherein the identifying the one or more backbone genomic regions may comprise maximizing a ranking function of sequencing load and utility associated with each of the backbone genomic regions; identifying one or more hotspot genomic regions of interest; creating a first bait set that selectively captures the backbone genomic regions of interest; and creating a second bait set that selectively captures the hot-spot genomic regions of interest. The second bait set may have a higher capture efficiency than the first bait set.

The one or more hot-spots may be selected using one or more of (e.g., one or more, two or more, three or more, or four of) the following: (i) maximizing a ranking function of sequencing load and utility associated with each of the hot-spot genomic regions, (ii) nucleosome profiling across the one or more genomic regions of interest, (iii) predetermined cancer driver mutations or prevalence across a relevant patient cohort, and (iv) empirically identified cancer driver mutations.

Identifying one or more hotspots of interest may comprise using a programmed computer processor to rank a set of hotspot genomic regions based on a ranking function of sequencing load and utility associated with each of the hotspot genomic regions. Identifying the one or more backbone genomic regions of interest may comprise ranking a set of backbone genomic regions based on a ranking function of sequencing load and utility associated with each of the backbone genomic regions of interest. Identifying the one or more hot-spot genomic regions of interest may comprise utilizing a set of empirically determined minor allele frequency (MAF) values or clonality of a variant measured by its MAF in relationship to the highest presumed driver or clonal mutation in a sample obtained from one or more subjects in a cohort of interest. Genomic regions that have relatively high MAF values in a cohort of interest may be suitable hotspots because they may indicate cancer-relevant assessments such as detection, cell type or tissue or origin, tumor burden, and/or treatment efficacy.

Sequencing load of a genomic region may be calculated by multiplying together one or more of (e.g., one or more, two or more, three or more, four or more, or five of) (i) size of the genomic region in base pairs, (ii) relative fraction of reads spent on sequencing fragments mapping to the genomic region, (iii) relative coverage as a result of sequence bias of the genomic region, (iv) relative coverage as a result of amplification bias of the genomic region, and (v) relative coverage as a result of capture bias of the genomic region. This indicator may be calculated for each genomic region in a bait panel set to identify the "costs" associated with generating sequence reads associated with the genomic region from a nucleic acid sample.

The sequencing load of a genomic region is linearly proportional to the size of the genomic region in base pairs. The relative fraction of reads spent on sequencing fragments mapping to the genomic region also influences the sequencing load of the genomic region, since some genomic regions may be especially difficult to sequence reliably (e.g., due to high GC-content or the presence of highly repeating sequences) and hence may require higher sequencing depth for analysis at the bait's desired resolution. Similarly relative coverage as a result of sequence bias, amplification bias, and/or capture bias of the genomic region may also affect the sequencing load of the genomic region. The total sequencing load of a given assay's sequencing run may then be calculated by summing all sequencing loads of the baits (including hot-spots and backbone regions) in the assay's selected bait panel set.

In some examples, utility of a genomic region may be calculated by multiplying together one or more of (e.g., one or more, two or more, three or more, four or more, five or more, six or more, or seven of) the following utility factors: (i) presence of one or more actionable mutations in the genomic region, (ii) frequency of one or more actionable mutations in the genomic region, (iii) presence of one or more mutations associated with above-average minor allele frequencies (MAFs) in the genomic region, (iv) frequency of one or more mutations associated with above-average MAFs in the genomic region, (v) fraction of patients in a cohort harboring a somatic mutation within the genomic region, (vi) sum of MAFs for variants in patients in a cohort, said patients harboring a somatic mutation within the genomic region, and (vii) ratio of (1) MAF for variants in patients in a cohort, said patients harboring a somatic mutation within the genomic region, to (2) maximum MAF for a given patient in the cohort.

The goal of calculating utility of a genomic region may be to help assess its relative importance for inclusion in a bait set panel. For example, the presence and/or frequency of one or more actionable mutations in the genomic region affect the utility of a genomic region for inclusion in a bait set panel, since genomic regions containing highly frequent mutations are good markers (e.g., indicators) of disease states including cancer. Similarly, the selection of genomic regions with presence and/or frequency of mutations associated with above-average MAFs will enable highly sensitive detection of these mutations in a liquid biopsy assay.

The fraction of patients in a cohort harboring a somatic mutation within the genomic region may indicate driver mutations that are suitable as a marker for the cohort's disease (e.g., breast, colorectal, pancreatic, prostate, melanoma, lung, or liver). To maximize the chances of detecting the highest MAF or driver variant, the sum of MAF for variants in patients in a cohort, said patients harboring a somatic mutation within the genomic region may be used as a utility factor. To give maximal weight to the driver mutations, the ratio of (1) MAF for variants in patients in a cohort, said patients harboring a somatic mutation within the genomic region, to (2) maximum MAF for a given patient in the cohort may be used as a utility factor. Mutations associated with higher minor allele frequencies may comprise one or more driver mutations or are known from external data or annotation sources.

Actionable mutations may comprise mutations whose detected presence may influence or determine clinical decisions (e.g., diagnosis, cancer monitoring, therapy monitoring, assessment of therapy efficacy). Actionable mutations may comprise one or more of (e.g., one or more, two or more, three or more, four or more, five or more, six or more, or seven of) (i) druggable mutations, (ii) mutations for therapeutic monitoring, (iii) disease specific mutations, (iv) tissue specific mutations, (v) cell type specific mutations, (vi) resistance mutations, and (vii) diagnostic mutations.

Druggable mutations may include those mutations whose detected presence in a nucleic acid sample from a subject may indicate that the subject is an appropriate candidate for treatment with a certain drug associated with the mutation (e.g., detection of EGFR L858R mutation may indicate the need to treat with a tyrosine kinase inhibitor (TKI) treatment). Mutations for therapeutic monitoring include those mutations whose detected presence or increased level in a nucleic acid sample from a subject may indicate that the subject's cancer is responding to a treatment course. Resistance mutations include those mutations whose detected presence or increased level in a nucleic acid sample from a subject may indicate that the subject's cancer has become resistant to a treatment course (e.g., emergence of EGFR T790M mutation may indicate the onset of resistance). Mutations may be specific to a disease (e.g., tumor type), tissue type, or cell type, whose detection may indicate cancer, inflammation, or another disease state in a particular organ, tissue, or cell type.

Exemplary listings of genomic locations of interest may be found in Table 3 and Table 4. In some embodiments, genomic regions used in the methods of the present disclosure comprise at least a portion of at least 5, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, or 97 of the genes of Table 3. In some embodiments, genomic regions used in the methods of the present disclosure comprise at least 5, at least 10, at least 15, at least 20, at least 25, at least 30, at least 35, at least 40, at least 45, at least 50, at least 55, at least 60, at least 65, or 70 of the SNVs of Table 3. In some embodiments, genomic regions used in the methods of the present disclosure comprise at least 1, at least 2, at least 3, at least 4, at least 5, at least 6, at least 7, at least 8, at least 9, at least 10, at least 11, at least 12, at least 13, at least 14, at least 15, at least 16, at least 17, or 18 of the CNVs of Table 3. In some embodiments, genomic regions used in the methods of the present disclosure comprise at least 1, at least 2, at least 3, at least 4, at least 5, or 6 of the fusions of Table 3. In some embodiments, genomic regions used in the methods of the present disclosure comprise at least a portion of at least 1, at least 2, or 3 of the indels of Table 3. In some embodiments, genomic regions used in the methods of the present disclosure comprise at least a portion of at least 5, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 105, at least 110, or 115 of the genes of Table 4. In some embodiments, genomic regions used in the methods of the present disclosure comprise at least 5, at least 10, at least 15, at least 20, at least 25, at least 30, at least 35, at least 40, at least 45, at least 50, at least 55, at least 60, at least 65, at least 70, or 73 of the SNVs of Table 4. In some embodiments, genomic regions used in the methods of the present disclosure comprise at least 1, at least 2, at least 3, at least 4, at least 5, at least 6, at least 7, at least 8, at least 9, at least 10, at least 11, at least 12, at least 13, at least 14, at least 15, at least 16, at least 17, or 18 of the CNVs of Table 4. In some embodiments, genomic regions used in the methods of the present disclosure comprise at least 1, at least 2, at least 3, at least 4, at least 5, or 6 of the fusions of Table 4. In some embodiments, genomic regions used in the methods of the present disclosure comprise at least a portion of at least 1, at least 2, at least 3, at least 4, at least 5, at least 6, at least 7, at least 8, at least 9, at least 10, at least 11, at least 12, at least 13, at least 14, at least 15, at least 16, at least 17, or 18 of the indels of Table 4. Each of these genomic locations of interest may be identified as a backbone region or hot-spot region for a given bait set panel. An exemplary listing of hot-spot genomic locations of interest may be found in Table 5. In some embodiments, genomic regions used in the methods of the present disclosure comprise at least a portion of at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, or at least 20 of the genes of Table 5. Each hot-spot genomic region is listed with several characteristics, including the associated gene, chromosome on which it resides, the start and stop position of the genome representing the gene's locus, the length of the gene's locus in base pairs, the exons covered by the gene, and the critical feature (e.g., type of mutation) that a given genomic region of interest may seek to capture.

TABLE 3

| Point Mutations (SNVs) | | | | | | Amplifications (CNVs) | | Fusions | Indels |
|---|---|---|---|---|---|---|---|---|---|
| AKT1 | ALK | APC | AR | ARAF | ARIDIA | AR | BRAF | ALK | EGFR |
| ATM | BRAF | BRCA1 | BRCA2 | CCND1 | CCND2 | CCND1 | CCND2 | FGFR2 | (exons |
| CCNE1 | CDH1 | CDK4 | CDK6 | CDKN2A | CDKN2B | CCNE1 | CDK4 | FGFR3 | 19 & 20) |
| CTNNB1 | EGFR | ERBB2 | ESR1 | EZH2 | FBXW7 | CDK6 | EGFR | NTRK1 | ERBB2 |
| FGFR1 | FGFR2 | FGFR3 | GATA3 | GNA11 | GNAQ | ERBB2 | FGFR1 | RET | (exons |
| GNAS | HNF1A | HRAS | IDH1 | IDH2 | JAK2 | FGFR2 | KIT | ROS1 | 19 & 20) |
| JAK3 | KIT | KRAS | MAP2K1 | MAP2K2 | MET | KRAS | MET | | MET |
| MLH1 | MPL | MYC | NF1 | NFE2L2 | NOTCH1 | MYC | PDGFRA | | (exon 14 |
| NPM1 | NRAS | NTRK1 | PDGFRA | PIK3CA | PTEN | PIK3CA | RAF1 | | skipping) |
| PTPN11 | RAF1 | RB1 | RET | RHEB | RHOA | | | | |
| RIT1 | ROS1 | SMAD4 | SMO | SRC | STK11 | | | | |
| TERT | TP53 | TSC1 | VHL | | | | | | |

TABLE 4

| Point Mutations (SNVs) | | | | | | Amplifications (CNVs) | | Fusions | Indels |
|---|---|---|---|---|---|---|---|---|---|
| AKT1 | ALK | APC | AR | ARAF | ARIDIA | AR | BRAF | ALK | EGFR |
| ATM | BRAF | BRCA1 | BRCA2 | CCND1 | CCND2 | CCND1 | CCND2 | FGFR2 | (exons |
| CCNE1 | CDH1 | CDK4 | CDK6 | CDKN2A | DDR2 | CCNE1 | CDK4 | FGFR3 | 19 & 20) |
| CTNNB1 | EGFR | ERBB2 | ESR1 | EZH2 | FBXW7 | CDK6 | EGFR | NTRK1 | ERBB2 |
| FGFR1 | FGFR2 | FGFR3 | GATA3 | GNA11 | GNAQ | ERBB2 | FGFR1 | RET | (exons |
| GNAS | HNF1A | HRAS | IDH1 | IDH2 | JAK2 | FGFR2 | KIT | ROS1 | 19 & 20) |
| JAK3 | KIT | KRAS | MAP2K1 | MAP2K2 | MET | KRAS | MET | | MET |
| MLH1 | MPL | MYC | NF1 | NFE2L2 | NOTCH1 | MYC | PDGFRA | | (exon 14 |
| NPM1 | NRAS | NTRK1 | PDGFRA | PIK3CA | PTEN | PIK3CA | RAF1 | | skipping) |
| PTPN11 | RAF1 | RB1 | RET | RHEB | RHOA | | | | ATM |
| RIT1 | ROS1 | SMAD4 | SMO | MAPK1 | STK11 | | | | |
| TERT | TP53 | TSC1 | VHL | MAPK3 | MTOR | | | | |
| NTRK3 | | | | | | | | | APC |
| | | | | | | | | | ARID1A |
| | | | | | | | | | BRCA1 |
| | | | | | | | | | BRCA2 |
| | | | | | | | | | CDH1 |
| | | | | | | | | | CDKN2A |

TABLE 4-continued

|  | Amplifications |  |  |
|---|---|---|---|
| Point Mutations (SNVs) | (CNVs) | Fusions | Indels |
|  | GATA3 |  |  |
|  | KIT |  |  |
|  | MLH1 |  |  |
|  | MTOR |  |  |
|  | NF1 |  |  |
|  | PDGFRA |  |  |
|  | PTEN |  |  |
|  | RB1 |  |  |
|  | SMAD4 |  |  |
|  | STK11 |  |  |
|  | TP53 |  |  |
|  | TSC1 |  |  |
|  | VHL |  |  |

TABLE 5

| Gene | Chromosome | Start Position | Stop Position | Length (bp) | Exons Covered | Critical Feature |
|---|---|---|---|---|---|---|
| ALK | chr2 | 29446405 | 29446655 | 250 | intron 19 | Fusion |
| ALK | chr2 | 29446062 | 29446197 | 135 | intron 20 | Fusion |
| ALK | chr2 | 29446198 | 29446404 | 206 | 20 | Fusion |
| ALK | chr2 | 29447353 | 29447473 | 120 | intron 19 | Fusion |
| ALK | chr2 | 29447614 | 29448316 | 702 | intron 19 | Fusion |
| ALK | chr2 | 29448317 | 29448441 | 124 | 19 | Fusion |
| ALK | chr2 | 29449366 | 29449777 | 411 | intron 18 | Fusion |
| ALK | chr2 | 29449778 | 29449950 | 172 | 18 | Fusion |
| BRAF | chr7 | 140453064 | 140453203 | 139 | 15 | BRAF V600 |
| CTNNB1 | chr3 | 41266007 | 41266254 | 247 | 3 | S37 |
| EGFR | chr7 | 55240528 | 55240827 | 299 | 18 and 19 | G719 and deletions |
| EGFR | chr7 | 55241603 | 55241746 | 143 | 20 | Insertions/T790M |
| EGFR | chr7 | 55242404 | 55242523 | 119 | 21 | L858R |
| ERBB2 | chr17 | 37880952 | 37881174 | 222 | 20 | Insertions |
| ESR1 | chr6 | 152419857 | 152420111 | 254 | 10 | V534, P535, L536, Y537, D538 |
| FGFR2 | chr10 | 123279482 | 123279693 | 211 | 6 | S252 |
| GATA3 | chr10 | 8111426 | 8111571 | 145 | 5 | SS/Indels |
| GATA3 | chr10 | 8115692 | 8116002 | 310 | 6 | SS/Indels |
| GNAS | chr20 | 57484395 | 57484488 | 93 | 8 | R844 |
| IDH1 | chr2 | 209113083 | 209113394 | 311 | 4 | R132 |
| IDH2 | chr15 | 90631809 | 90631989 | 180 | 4 | R140, R172 |
| KIT | chr4 | 55524171 | 55524258 | 87 | 1 |  |
| KIT | chr4 | 55561667 | 55561957 | 290 | 2 |  |
| KIT | chr4 | 55564439 | 55564741 | 302 | 3 |  |
| KIT | chr4 | 55565785 | 55565942 | 157 | 4 |  |
| KIT | chr4 | 55569879 | 55570068 | 189 | 5 |  |
| KIT | chr4 | 55573253 | 55573463 | 210 | 6 |  |
| KIT | chr4 | 55575579 | 55575719 | 140 | 7 |  |
| KIT | chr4 | 55589739 | 55589874 | 135 | 8 |  |
| KIT | chr4 | 55592012 | 55592226 | 214 | 9 |  |
| KIT | chr4 | 55593373 | 55593718 | 345 | 10 and 11 | 557, 559, 560, 576 |
| KIT | chr4 | 55593978 | 55594297 | 319 | 12 and 13 | V654 |
| KIT | chr4 | 55595490 | 55595661 | 171 | 14 | T670, S709 |
| KIT | chr4 | 55597483 | 55597595 | 112 | 15 | D716 |
| KIT | chr4 | 55598026 | 55598174 | 148 | 16 | L783 |
| KIT | chr4 | 55599225 | 55599368 | 143 | 17 | C809, R815, D816, L818, D820, S821F, N822, Y823 |
| KIT | chr4 | 55602653 | 55602785 | 132 | 18 | A829P |
| KIT | chr4 | 55602876 | 55602996 | 120 | 19 |  |
| KIT | chr4 | 55603330 | 55603456 | 126 | 20 |  |
| KIT | chr4 | 55604584 | 55604733 | 149 | 21 |  |
| KRAS | chr12 | 25378537 | 25378717 | 180 | 4 | A146 |
| KRAS | chr12 | 25380157 | 25380356 | 199 | 3 | Q61 |
| KRAS | chr12 | 25398197 | 25398328 | 131 | 2 | G12/G13 |
| MET | chr7 | 116411535 | 116412255 | 720 | 13, 14, intron 13, intron 14 | MET exon 14 SS |
| NRAS | chr1 | 115256410 | 115256609 | 199 | 3 | Q61 |
| NRAS | chr1 | 115258660 | 115258791 | 131 | 2 | G12/G13 |
| PIK3CA | chr3 | 178935987 | 178936132 | 145 | 10 | E545K |
| PIK3CA | chr3 | 178951871 | 178952162 | 291 | 21 | H1047R |
| PTEN | chr10 | 89692759 | 89693018 | 259 | 5 | R130 |
| SMAD4 | chr18 | 48604616 | 48604849 | 233 | 12 | D537 |

TABLE 5-continued

| Gene | Chromosome | Start Position | Stop Position | Length (bp) | Exons Covered | Critical Feature |
|---|---|---|---|---|---|---|
| TERT | chr5 | 1294841 | 1295512 | 671 | promoter | chr5:1295228 |
| TP53 | chr17 | 7573916 | 7574043 | 127 | 11 | Q331, R337, R342 |
| TP53 | chr17 | 7577008 | 7577165 | 157 | 8 | R273 |
| TP53 | chr17 | 7577488 | 7577618 | 130 | 7 | R248 |
| TP53 | chr17 | 7578127 | 7578299 | 172 | 6 | R213/Y220 |
| TP53 | chr17 | 7578360 | 7578564 | 204 | 5 | R175/Deletions |
| TP53 | chr17 | 7579301 | 7579600 | 299 | 4 | |
| | | | | 12574 (total target region) | | |
| | | | | 16330 (total probe coverage) | | |

In an aspect, a bait panel may comprise a plurality of bait sets, each bait set (i) comprising one or more baits that selectively capture one or more genomic regions with utility in the same quantile across the plurality of baits, and (ii) having a different relative concentration from each of the other bait sets with utility in a different quantile across the plurality of baits. Quantiles may be, for example, two halves, three thirds, four quarters, etc. For example, a bait panel may comprise three bait sets, each bait set comprising baits that selectively capture genomic regions with utility in the upper third, middle third, or lower third of utility values across the plurality of baits, with each of the three bait sets having a different relative concentration.

A bait panel may comprise a plurality of bait sets, each bait set (i) comprising one or more baits that selectively capture one or more genomic regions with sequencing load in the same quantile across the plurality of baits, and (ii) having a different relative concentration from each of the other bait sets with sequencing load in a different quantile across the plurality of baits. A bait panel may comprise a plurality of bait sets, each bait set (i) comprising one or more baits that selectively capture one or more genomic regions with ranking function value (e.g., utility divided by sequencing load) in the same quantile across the plurality of baits, and (ii) having a different relative concentration from each of the other bait sets with ranking function value in a different quantile across the plurality of baits.

In an aspect, a method of selecting a set of panel blocks may comprise (a) for each panel block, (i) calculating a utility of the panel block, (ii) calculating a sequencing load of the panel block, and (iii) calculating a ranking function of the panel block; and (b) performing an optimization process to select a set of panel blocks that maximizes the total ranking function values of the selected panel blocks. A ranking function of a panel block may be calculated as the utility of a panel block divided by the sequencing load of a panel block. The combinatorial optimization process may optimize the total sum of ranking function values of all panel blocks selected for the set of panel blocks in a single assay. This approach may enable an optimal panel selection given constraints in sequence load and utility. The combinatorial optimization process may be a greedy algorithm. In an aspect, a method may comprise (a) providing a plurality of bait mixtures, wherein each of the plurality of bait mixtures comprises a first bait set that selectively hybridizes to a first set of genomic regions and a second bait set that selectively hybridizes to a second set of genomic regions, wherein the first bait set is at different concentrations across the plurality of bait mixtures and the second bait set is at the same concentration across the plurality of bait mixtures; (b) contacting each of the plurality of bait mixture with a nucleic acid sample to capture nucleic acids from the nucleic acid sample with the first bait set and the second bait set, wherein the nucleic acids from the nucleic acid samples are capture by the first bait set and the second bait set; (c) sequencing a portion of the nucleic acids captured with each bait mixture to produce sets of sequence reads within an allocated number of sequence reads; (d) determining the read depth for the first bait set and the second bait set for each bait mixture; and (e) identifying at least one bait mixture that provides read depths for the second set of genomic regions and, optionally, first set of genomic regions, at predetermined amounts. In some embodiments, the read depths for the second set of genomic regions provides a sensitivity of detecting a genetic variant of at least 0.0001% MAF. In some embodiments, a first set of genomic regions and/or a second set of regions have a size between 25 kilobases to 1,000 kilobases. In some embodiments, a first set of genomic regions and/or a second set of regions have a read depth of between 1,000 counts/base and 50,000 counts/base.

Improved Accuracy of Indel Detection

A method is disclosed for improving accuracy of detecting an insertion or deletion (indel) from a plurality of sequence reads derived from cell-free deoxyribonucleic acid (cfDNA) molecules in a bodily sample of a subject, which plurality of sequence reads are generated by nucleic acid sequencing. For each of the plurality of sequence reads associated with cfDNA molecules, a candidate indel may be identified. Each candidate indel may then be classified as either a true indel or an introduced indel, using a combination of predetermined expectations of (i) an indel being detected in one or more sequence reads of the plurality of sequence reads, (ii) that a detected indel is a true indel present in a given cell-free DNA molecule of the cell-free DNA molecules, given that an indel has been detected in the one or more of the sequence reads, and/or (iii) that a detected indel is introduced by non-biological error, given that an indel has been detected in the one or more of the sequence reads, in conjunction with one or more model parameters to perform a hypothesis test. This approach may reduce error and improve accuracy of detecting an indel from sequence read data.

FIG. 1 illustrates how a plurality of reads may be generated for each locus enriched from a cell-free nucleic acid sample. Each enriched nucleic acid molecule (e.g., DNA molecule) is amplified to produce a family of amplicons. These amplicons may then be sequenced on both forward and reverse strands to produce a plurality of sequence read data. From the plurality of sequence read data, candidate indels may be detected and classified as either true indels or introduced (e.g., non-biological) indels.

This algorithm presumes that for any given DNA molecule for which a plurality of sequence reads is analyzed for variants comprising indels, there exists a predetermined expectation (e.g., probability) of an indel being present either in the original molecule (e.g., a "true" biological indel) or introduced at some point in a protocol that culminates a set of sequence reads (e.g., an introduced non-biological indel stemming from error, including amplification or sequencing error). The model may aim to perform a hypothesis test which asks, given a pattern of reads mapping to a particular base position (e.g., cover the base position somewhere in the read), if the observed pattern is most indicative of an indel in a sequence being present at the beginning of the protocol (e.g., a true biological indel) or introduced during the protocol (a non-biological indel).

In an aspect, a method for improving accuracy of detecting an insertion or deletion (indel) from a plurality of sequence reads derived from cell-free deoxyribonucleic acid (cfDNA) molecules in a bodily sample of a subject, which plurality of sequence reads are generated by nucleic acid sequencing, may comprise (a) for each of the plurality of sequence reads associated with the cell-free DNA molecules, providing: a predetermined expectation of an indel being detected in one or more sequence reads of the plurality of sequence reads; a predetermined expectation that a detected indel is a true indel present in a given cell-free DNA molecule of the cell-free DNA molecules, given that an indel has been detected in the one or more of the sequence reads; and a predetermined expectation that a detected indel is introduced by non-biological error, given that an indel has been detected in the one or more of the sequence reads; (b) providing quantitative measures of one or more model parameters characteristic of sequence reads generated by nucleic acid sequencing; (c) detecting one or more candidate indels in the plurality of sequence reads associated with the cell-free DNA molecules; and (d) for each candidate indel, performing a hypothesis test using one or more of the model parameters to classify said candidate indel as a true indel or an introduced indel, thereby improving accuracy of detecting an indel.

The method for improving accuracy of detecting an insertion or deletion (indel) from a plurality of sequence reads derived from cell-free deoxyribonucleic acid (cfDNA) molecules in a bodily sample of a subject may further comprise enriching one or more loci from the cell-free DNA in the bodily sample before step (a), thereby producing enriched polynucleotides.

The method may further comprise amplifying the enriched polynucleotides to produce families of amplicons, wherein each family comprises amplicons originating from a single strand of the cell-free DNA molecules. The non-biological error may comprise error in sequencing at a plurality of genomic base locations. The non-biological error may comprise error in amplification at a plurality of genomic base locations.

Figure 2:
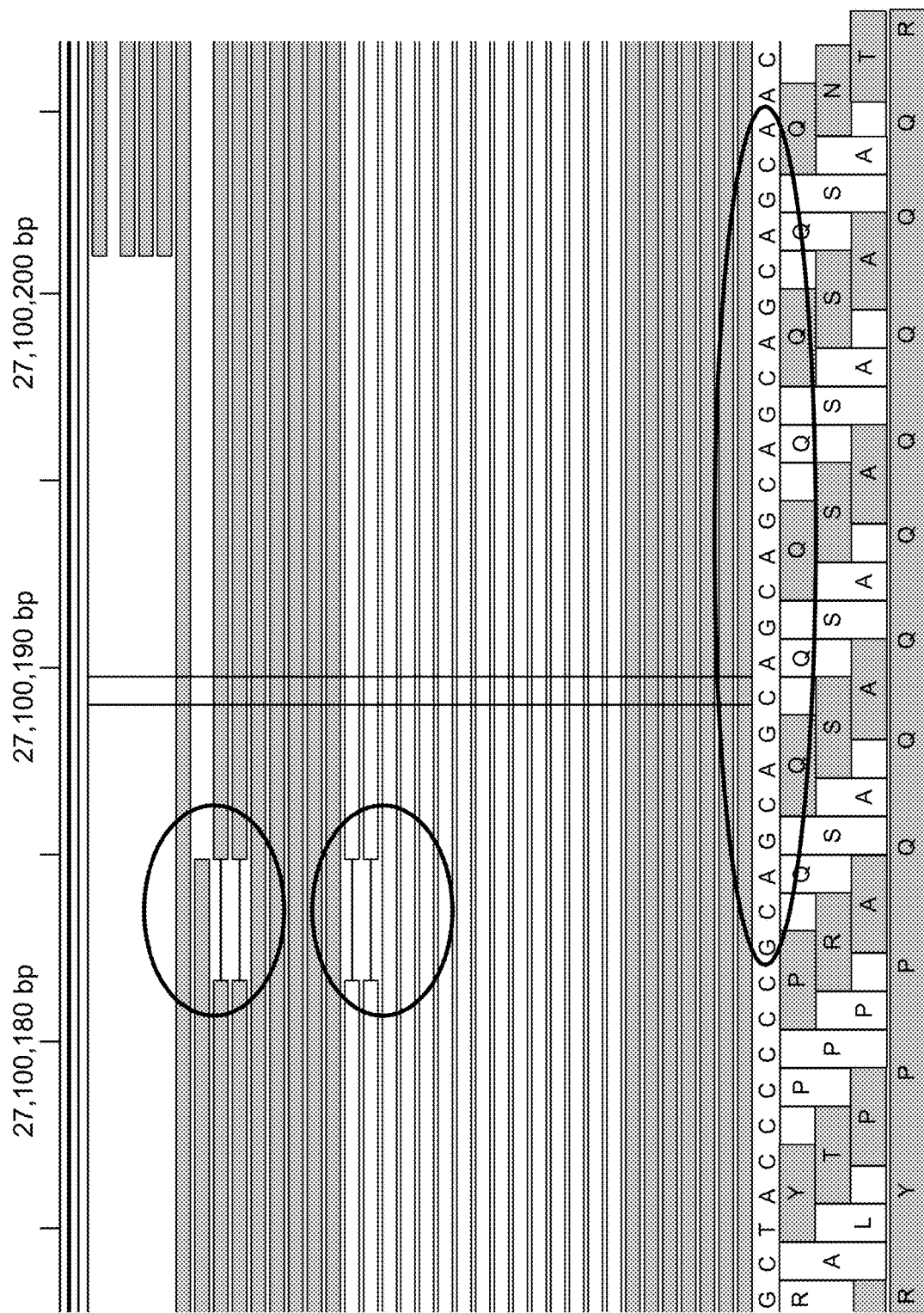
FIG. 2 illustrates an example of an insertion being supported by a large family.

FIG. 2 illustrates an example of small families of reads (which may appear to provide evidence for a true indel variant) and large families of reads (which may indicate a likely introduced error stemming from PCR or sequencing. In general, true indels may be expected to be detected or measured as small families of reads, since they may not be expected to affect large numbers of DNA molecules biologically. In contrast, introduced indels may be expected to be detected or measured as larger families of reads, which may indicate an introduced error during PCR or sequencing.

Some untrimmed or erroneous reads may cause the algorithm to disqualify the family based on a hypothesis test that classifies an indel (e.g., insertion or deletion) as introduced rather than biological.

Figure 3:
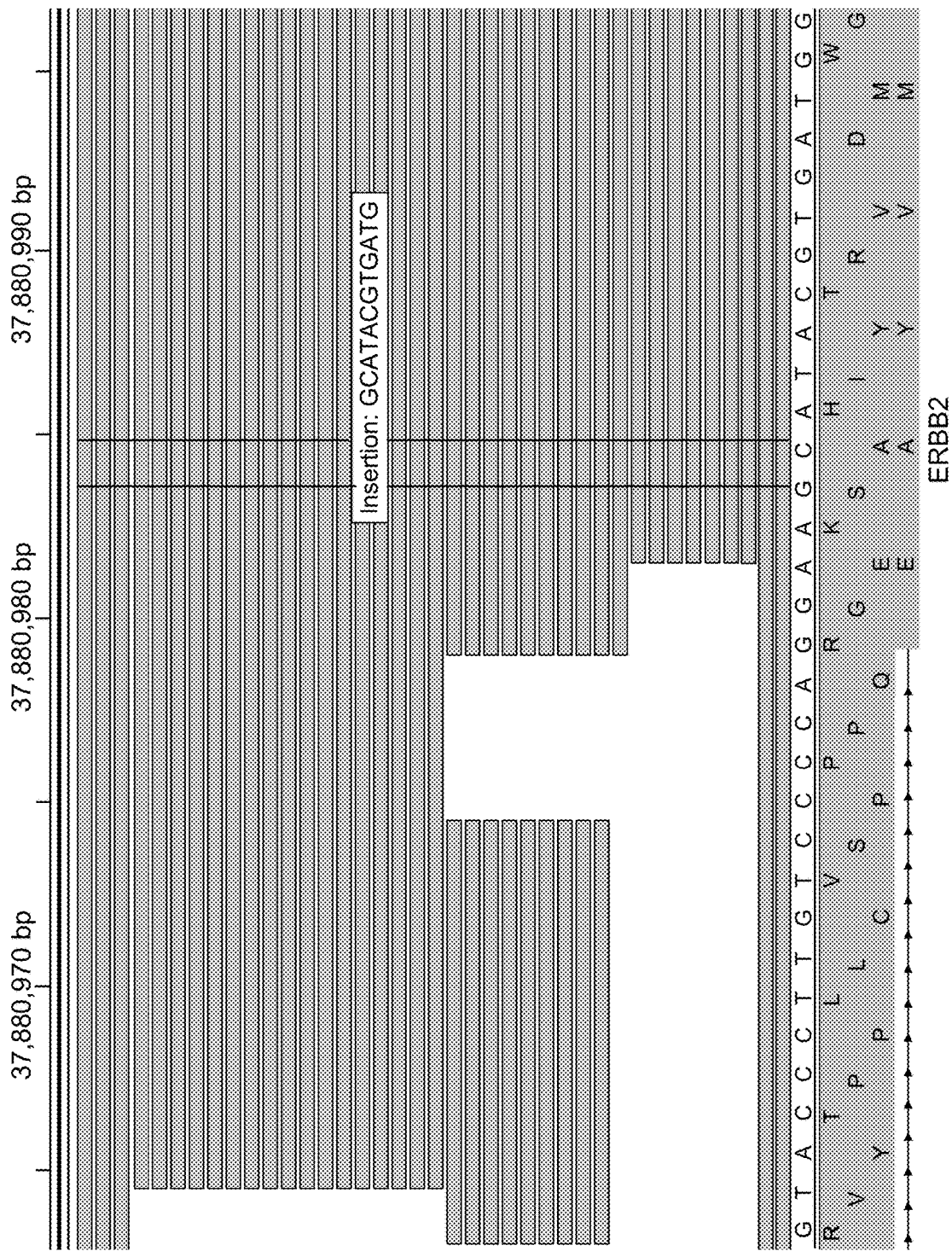
FIG. 3 illustrates an example of small families of reads (which may appear to provide evidence for a real variant) and large families of reads (which may indicate a likely random error stemming from PCR or sequencing.

FIG. 3 illustrates an example of an insertion being supported by a large family upon aligning and comparing a plurality of sequence reads to a reference genome. As in the above case in FIG. 3, some untrimmed or erroneous reads may cause the algorithm to disqualify the family based on a hypothesis test that classifies an indel (e.g., insertion or deletion) as introduced rather than biological.

Model parameters may comprise one or more of (e.g., one or more, two or more, three or more, or four of) (i) for each of one or more variant alleles, a frequency of the variant allele ($\alpha$) and a frequency of non-reference alleles other than the variant allele ($\alpha'$); (ii) a frequency of an indel error in the entire forward strand of a family of strands ($\beta_1$), wherein a family comprises a collection of amplicons originating from a single strand of the cell-free DNA molecules; (iii) a frequency of an indel error in the entire reverse strand of a family of strands ($\beta_2$); and (iv) a frequency of an indel error in a sequence read ($\gamma$).

Figure 4:
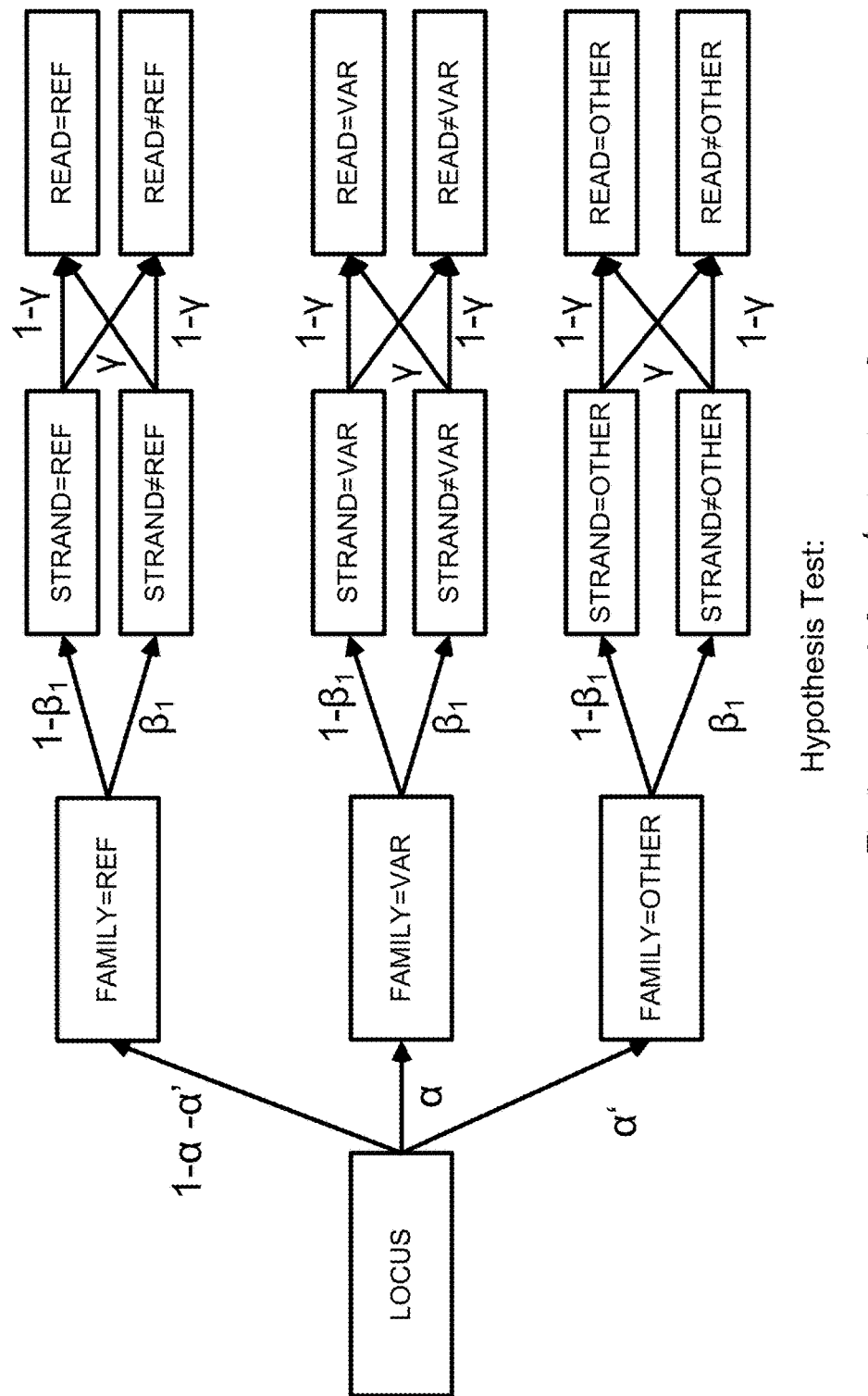
FIG. 4 illustrates the various parameters that may be used in a hypothesis test and how each parameter may be related to a particular probability, e.g., of a family of reads matching a reference, of a strand's reads matching a reference, and of a read matching a reference.

FIG. 4 illustrates the various parameters that may be used in a hypothesis test and how each parameter may be related to a particular probability, e.g., of a family of reads matching a reference, of a strands' reads matching a reference, and of a read matching a reference. FIG. 2 also illustrates how a parameter test containing a maximum likelihood function may be performed. If the parameter test is greater than a predetermined threshold when performed on a candidate indel, then the candidate may be classified as a true indel. If the parameter test is less than or equal to a predetermined threshold when performed on a candidate indel, then the candidate may be classified as an introduced (e.g., non-biological) indel.

The step of performing a hypothesis test may comprise performing a multi-parameter maximization algorithm. The multi-parameter maximization algorithm may comprise a Nelder-Mead algorithm. The classifying of a candidate indel as a true indel or an introduced indel may comprise (a) maximizing a multi-parameter likelihood function, (b) classifying a candidate indel as a true indel if the maximum likelihood function value is greater than a predetermined threshold value, and (c) classifying a candidate indel as an introduced indel if the maximum likelihood function value is less than or equal to a predetermined threshold value. The multi-parameter likelihood function may be given as:

$$Pr\{\text{Reads} \mid \alpha, \alpha', \beta_1, \beta_2, \gamma\} =$$
$$\prod_{Families} \left(\alpha \cdot \left((1-\beta_1)(1-\gamma)R_{1\gamma}^{Y_1+O_1} + \beta_1\gamma^{R_1}(1-\gamma)^{Y_1+O_1}\right) \cdot \right.$$
$$\left.\left((1-\beta_2)(1-\gamma)R_{2\gamma}^{Y_2+O_2} + \beta_2\gamma^{R_2}(1-\gamma)^{Y_2-O_2}\right) + \alpha' \cdot (\ldots) + (1-\alpha-\alpha') \cdot (\ldots)\right)$$

A multi-parameter likelihood function Pr{Reads|$\alpha$, $\alpha'$, $\beta_1$, $\beta_2$, $\gamma$} may represent a probability of an observed configuration of reads according to the model illustrated in FIG. 4 (and described in paragraph [00112]). One assumption of the model may be that, given certain values of parameters (e.g., $\alpha$, $\alpha'$, $\beta_1$, $\beta_2$, and $\gamma$), an observed configuration of reads within a family is statistically independent from an observed configuration of reads within all other families. Therefore, the probability Pr{Reads|$\alpha$, $\alpha'$, $\beta_1$, $\beta_2$, $\gamma$} can be expressed as a product of Pr{reads in family f|$\alpha$, $\alpha'$, $\beta_1$, $\beta_2$, $\gamma$} over all families. This per-family probability itself may comprise a weighted sum of at least three components, wherein each component corresponds to a possible family type: a) having the variant allele (with weight $\alpha$), b) having other non-reference variant allele (with weight $\alpha'$, or c) having the reference allele (with weight $1-\alpha-\alpha'$). These components being summed may be probabilities of observed read configuration for the respective family type Pr{reads in family f|$\alpha$, $\alpha'$, $\beta_1$, $\beta_2$, $\gamma$, and family f having variant allele}, Pr{reads in family f|$\alpha$, $\alpha'$, $\beta_1$, $\beta_2$, $\gamma$, and family f having other non-reference variant allele}, and Pr{reads in family f|$\alpha$, $\alpha'$, $\beta_1$, $\beta_2$, $\gamma$, and family f having reference allele}.

Since the model postulates that within a family each strand may be affected by an indel error independently of the other strand, the probability of observed read configuration for a family having variant allele Pr{reads in family f|$\alpha$, $\alpha'$, $\beta_1$, $\beta_2$, $\gamma$, and family f having variant allele} may be itself a product of the probability of observed configuration of reads from the forward strand and the probability of observed configuration of reads from the reverse strand. Each of these probabilities may be itself a weighted sum of at least two components, wherein each component corresponds to a possible outcome: X) the strand-specific indel error did affect this family strand (with weight $\beta_1$ or $\beta_2$) and Y) the strand-specific indel error did not affect this family strand (with weight $1-\beta_1$ or $1-\beta_2$).

Finally, within a family of assumed type a), b), or c), and/or within a strand of assumed type X) or Y), the probability of a specific read configuration may be a product of probabilities for individual reads, since it is postulated by the model that these reads have a statistically independent probability of falling into one of the three categories: i) read supports the variant allele, ii) read supports other non-reference variant allele, or iii) read supports the reference allele. These probabilities are listed in Table 6 below.

TABLE 6

| Family | Strand error | i) read supports variant | ii) read supports other | iii) read supports reference |
|---|---|---|---|---|
| a) variant allele | present | $\gamma$ | $1-\gamma$ | $1-\gamma$ |
|  | absent | $1-\gamma$ | $\gamma$ | $\gamma$ |
| b) other variant allele | present | $1-\gamma$ | $\gamma$ | $1-\gamma$ |
|  | absent | $\gamma$ | $1-\gamma$ | $\gamma$ |
| c) reference allele | present | $1-\gamma$ | $1-\gamma$ | $\gamma$ |
|  | absent | $\gamma$ | $\gamma$ | $1-\gamma$ |

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

Computer Control Systems

The present disclosure provides computer control systems that are programmed to implement methods of the disclosure. In one aspect, the present disclosure provides a system comprising a computer comprising a processor and computer memory, wherein the computer is in communication with a communications network, and wherein computer memory comprises code which, when executed by the processor, (1) receives sequence data into computer memory from the communications network; (2) determines whether a genetic variant in the sequence data represents a mutant; and (3) reports out, over the communications network, the determination.

A communications network can be any available network that connects to the Internet. The communications network can utilize, for example, a high-speed transmission network including, without limitation, Broadband over Powerlines (BPL), Cable Modem, Digital Subscriber Line (DSL), Fiber, Satellite and Wireless.

In another aspect provided herein a system comprising: a local area network; one or more DNA sequencers comprising computer memory configured to store DNA sequence data which are connected to the local area network; a bioinformatics computer comprising a computer memory and a processor, which computer is connected to the local area network; wherein the computer further comprises code which, when executed, copies DNA sequence data stored on the DNA sequencer, writes the copied data to memory in the bioinformatics computer and performs steps as described herein.

Figure 5:
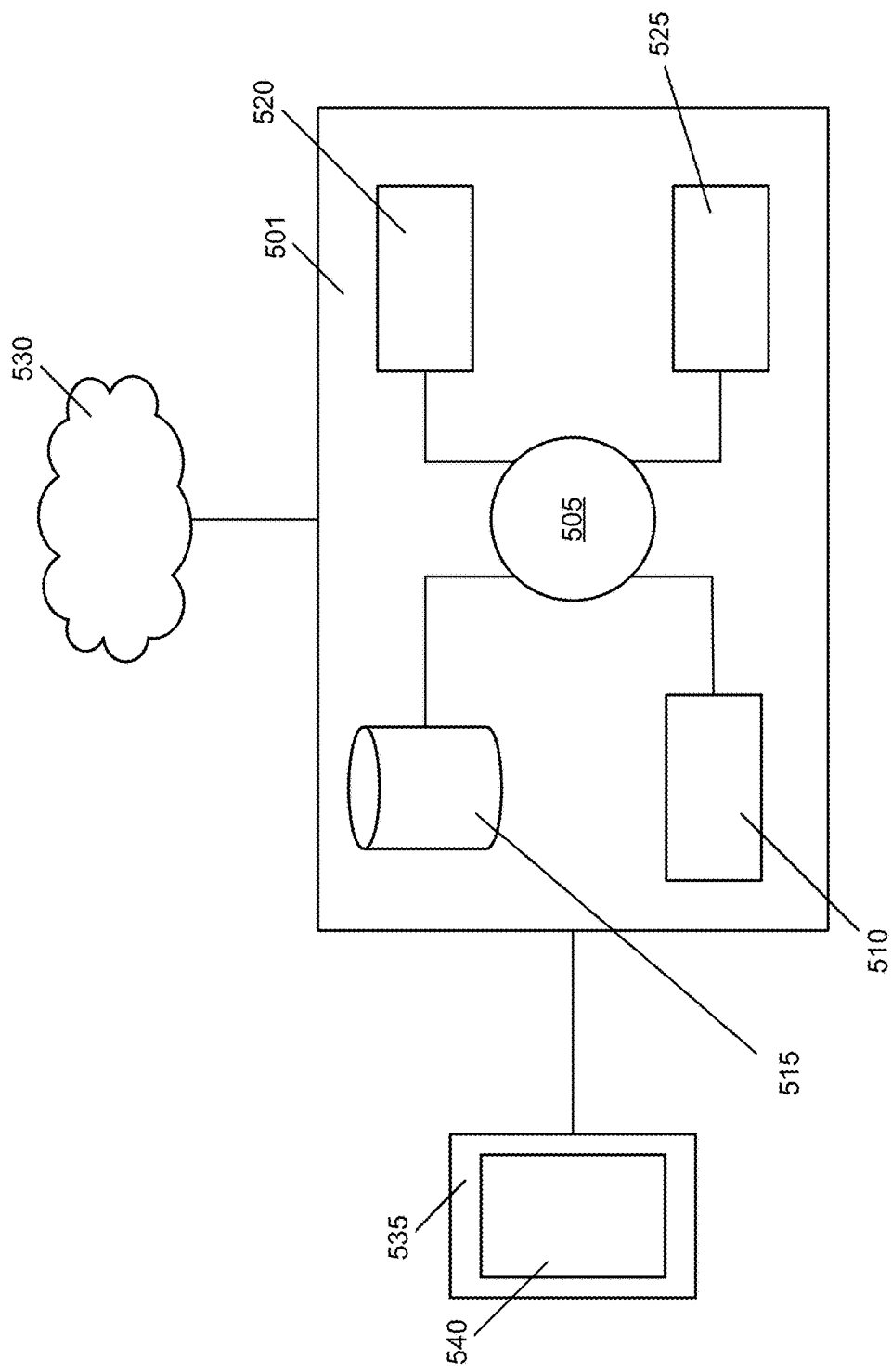
FIG. 5 illustrates an example of a computer system that may be programmed or otherwise configured to implement methods of the present disclosure.

FIG. 5 shows a computer system 501 that is programmed or otherwise configured to implements methods for generating a bait set, for selecting a set of panel blocks, and for improving accuracy of detecting an indel from a plurality of sequence reads derived from cfDNA molecules. The computer system 501 can regulate various aspects of the present disclosure, such as, for example, methods for generating a bait set, for selecting a set of panel blocks, or for improving accuracy of detecting an indel from a plurality of sequence reads derived from cfDNA molecules. The computer system 501 can be an electronic device of a user or a computer system that is remotely located with respect to the electronic device. The electronic device can be a mobile electronic device.

The computer system 501 includes a central processing unit (CPU, also "processor" and "computer processor" herein) 505, which can be a single core or multi core processor, or a plurality of processors for parallel processing. The computer system 501 also includes memory or memory location 510 (e.g., random-access memory, read-only memory, flash memory), electronic storage unit 515 (e.g., hard disk), communication interface 520 (e.g., network adapter) for communicating with one or more other systems, and peripheral devices 525, such as cache, other memory, data storage and/or electronic display adapters. The memory 510, storage unit 515, interface 520 and peripheral devices 525 are in communication with the CPU 505 through a communication bus (solid lines), such as a motherboard. The storage unit 515 can be a data storage unit (or data repository) for storing data. The computer system 501 can be operatively coupled to a computer network ("network") 530 with the aid of the communication interface 520. The network 530 can be the Internet, an internet and/or extranet, or an intranet and/or extranet that is in communication with the Internet. The network 530 in some cases is a telecommunication and/or data network. The network 530 can include one or more computer servers, which can enable distributed computing, such as cloud computing. The network 530, in some cases with the aid of the computer system 501, can implement a peer-to-peer network, which may enable devices coupled to the computer system 501 to behave as a client or a server.

The CPU 505 can execute a sequence of machine-readable instructions, which can be embodied in a program or software. The instructions may be stored in a memory location, such as the memory 510. The instructions can be directed to the CPU 505, which can subsequently program or otherwise configure the CPU 505 to implement methods of the present disclosure. Examples of operations performed by the CPU 505 can include fetch, decode, execute, and writeback.

The CPU 505 can be part of a circuit, such as an integrated circuit. One or more other components of the system 501 can be included in the circuit. In some cases, the circuit is an application specific integrated circuit (ASIC).

The storage unit 515 can store files, such as drivers, libraries and saved programs. The storage unit 515 can store user data, e.g., user preferences and user programs. The computer system 501 in some cases can include one or more additional data storage units that are external to the computer system 501, such as located on a remote server that is in communication with the computer system 501 through an intranet or the Internet.

The computer system 501 can communicate with one or more remote computer systems through the network 530. For instance, the computer system 501 can communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 501 via the network 530.

Methods as described herein can be implemented by way of machine (e.g., computer processor) executable code stored on an electronic storage location of the computer system 501, such as, for example, on the memory 510 or electronic storage unit 515. The machine executable or machine readable code can be provided in the form of software. During use, the code can be executed by the processor 505. In some cases, the code can be retrieved from the storage unit 515 and stored on the memory 510 for ready access by the processor 505. In some situations, the electronic storage unit 515 can be precluded, and machine-executable instructions are stored on memory 510.

The code can be pre-compiled and configured for use with a machine having a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 501, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 501 can include or be in communication with an electronic display 535 that comprises a user interface (UI) 540 for providing, for example, input parameters for methods for generating a bait set, for selecting a set of panel blocks, or for improving accuracy of detecting an indel from a plurality of sequence reads derived from cfDNA. Examples of UIs include, without limitation, a graphical user interface (GUI) and web-based user interface.

Methods and systems of the present disclosure can be implemented by way of one or more algorithms. An algorithm can be implemented by way of software upon execution by the central processing unit 505. The algorithm can, for example, generate a bait set, select a set of panel blocks, or improve accuracy of detecting an indel from a plurality of sequence reads derived from cfDNA molecules.

EXAMPLES

Example 1: Analytical Performance Assessment

Analytical sensitivity (as defined by the limit of detection and by positive percent agreement) and precision were assessed throughout the reportable allelic fraction and copy number ranges via multiple serial dilution studies of orthogonally-characterized contrived material and patient samples. Analytical specificity was assessed by calculating the false positive rate in pre-characterized healthy donor sample mixtures serially diluted across the lower reportable range down to allelic fractions below the limit of detection. Positive predictive value (PPV) was estimated as a function of allelic fraction/copy number from pre-characterized clinical patient samples and prevalence-adjusted using a cohort of 2,585 consecutive clinical samples. Orthogonal qualitative and quantitative confirmation was performed using ddPCR.

Analytical performance is summarized in Table 7 below. Analytical specificity was 100% for single nucleotide variants (SNVs), fusions, and copy number alterations (CNAs) and 96% (24/25) for indels across 25 defined samples. Relative to other methods, this assay demonstrated 20%-50% increases in fusion molecule recovery, depending on the sequence context. Retrospective in silico analysis of 2,585 consecutive clinical samples demonstrated a >15% relative increase in actionable fusion detection, a 6%-15% increase in actionable indel detection (excluding newly reportable indels), and a 3%-6% increase in actionable SNV detection.

Table 7: Analytical performance characteristics based on standard cfDNA input (30 ng). Analytical sensitivity/limit of detection estimates are provided for clinically actionable variants and can vary by sequence context and cfDNA input. Positive predictive value is estimated across the entire reportable panel space (PPV was 100% for clinically actionable variants).

In sum, the assay comprehensively detected all adult solid tumor guideline-recommended somatic genomic variants with high sensitivity, accuracy, and specificity.

Example 2: Hotspot and Backbone Titration

In this experiment, the appropriate probe replication and the saturation point for each panel were determined. Hotspot and backbone panels were designed for both default probe replication and optimized probe replication. The hotspot panel is approximately 12 kb and targets regions of genomic targets that may be indicative of drug response, a disease status (e.g., cancer), and/or a genomic target listed under National Comprehensive Cancer Network ("NCCN") guidelines. The backbone panel is approximately 140 kb and covers the rest of the panel content. The hotspot and backbone panel may comprise any genetic locations in Table 3. A titration experiment was performed for panel input amount for each of the four panels at 5 ng, 15 ng, and 30 ng of cfDNA as set forth in Table 1. FIG. 6 shows input amount versus unique molecule count for the generic panel. The unique molecule count saturated at about Vol. 3× for the backbone bait and about Vol. 1.2× for the hotspot bait (data not shown), suggesting that the optimized backbone panel was less variable compared to the default panel.

Example 3: Selective Capturing of a Hotspot Region

Based on the saturation point of each panel in Example 2, a concentration of backbone bait and a concentration of hotspot bait were determined. A mixture of backbone bait (e.g., Vol. A) and hotspot bait (e.g., Vol. B) was generated and the molecule count for the hotspot/backbone bait mixture was compared with molecule count for a generic panel. The molecule counts from the hotspot panel were higher than the backbone panel. The difference became more noticeable at higher cfDNA input amount as the backbone bait saturated out much faster, e.g., at lower input amount, as compared to the hotspot bait. A similar trend was seen with the double-stranded count (data not shown). Family size was also higher for the hotspot panel than the backbone panel (data not shown). The difference in family sizes may indicate that the hotspot panel is capturing more than the backbone panel, despite that the effect was masked with molecule counts. For example, with the large family sizes for 5 ng, it is likely that most of the unique molecules were captured, thus there was no obvious difference between the

TABLE 7

| Alterations | Reportable Range | 95% Limit of Detection | Allelic Fraction/ Copy Number | Analytical Sensitivity | Allelic Fraction/Copy number | PPV |
| --- | --- | --- | --- | --- | --- | --- |
| SNVs | ≥0.04% | 0.25% | ≥0.25% | >99.9% | ≥0.25% | 98.7% |
|  |  |  | 0.05-0.25% | 63.8% | <0.25% | 92.3% |
| Indels | ≥0.02% | 0.2% | ≥0.25% | >99.9% | ≥0.25% | 98.4% |
|  |  |  | 0.05-0.25% | 67.8% | <0.25% | 88.5% |
| Fusions | ≥0.04% | 0.4% | ≥0.3% | 100% | any | 100% |
|  |  |  | <0.3% | 83.0% |  |  |
| CNAs | ≥2.12 copies | 2.24-2.93 copies | 2.3 copies | 95.0% | any | 100% | hotspot and backbone panel. With the family size differences, it is likely that more PCR duplicates were being captured by the hotspot panel than the backbone panel.

In sum, this experiment demonstrates that hotspot regions may be selectively captured with an increased hotspot panel amount.

```
                              SEQUENCE LISTING

Sequence total quantity: 11
SEQ ID NO: 1            moltype = DNA  length = 36
FEATURE                 Location/Qualifiers
misc_feature            1..36
                        note = Description of Artificial Sequence: Synthetic
                         oligonucleotide
source                  1..36
                        mol_type = other DNA
                        organism = synthetic construct
SEQUENCE: 1
gctacccccc gcagcagcag cagcagcagc agcaac                                    36

SEQ ID NO: 2            moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 2
RYPPQQQQQQ QQ                                                              12

SEQ ID NO: 3            moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 3
ATPRSSSSSS SN                                                              12

SEQ ID NO: 4            moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 4
LPPAAAAAAA AT                                                              12

SEQ ID NO: 5            moltype = AA  length = 13
FEATURE                 Location/Qualifiers
REGION                  1..13
                        note = Description of Artificial Sequence: Synthetic peptide
source                  1..13
                        mol_type = protein
                        organism = synthetic construct
SEQUENCE: 5
RYPPQQQQQQ QQR                                                             13

SEQ ID NO: 6            moltype = DNA  length = 12
FEATURE                 Location/Qualifiers
misc_feature            1..12
                        note = Description of Artificial Sequence: Synthetic
                         oligonucleotide
source                  1..12
                        mol_type = other DNA
                        organism = synthetic construct
SEQUENCE: 6
gcatacgtga tg                                                              12

SEQ ID NO: 7            moltype = DNA  length = 32
FEATURE                 Location/Qualifiers
misc_feature            1..32
                        note = Description of Artificial Sequence: Synthetic
                         oligonucleotide
source                  1..32
                        mol_type = other DNA
                        organism = synthetic construct
SEQUENCE: 7
gtacccttgt ccccaggaag catacgtgat gg                                        32
```

```
SEQ ID NO: 8            moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 8
RTLVPRKHT                                                                      9

SEQ ID NO: 9            moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 9
VPLSPGSIRD G                                                                  11

SEQ ID NO: 10           moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 10
YPCPQEAYVM                                                                    10

SEQ ID NO: 11           moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 11
EAYVM                                                                          5
```

What is claimed is:

1. A method for multi-resolution analysis of cell-free DNA (cfDNA) comprising:
   (a) providing a sample comprising cfDNA;
   (b) enriching cfDNA, or amplification products thereof, from hotspot regions and backbone regions, using a bait set panel which preferentially enriches for the hotspot regions compared to the backbone regions to provide an enriched set of nucleic acids, wherein the backbone regions are larger genomic regions compared to the genomic regions of the hotspot regions; and
   (c) sequencing the enriched set of nucleic acids, or amplification products thereof, wherein the enrichment results in higher average read depth for the hotspot regions compared to the average read depth for the backbone regions, wherein the hotspot regions and/or the backbone regions are sequenced to a read depth of between 1,000 counts/base and 50,000 counts/base.

2. The method of claim 1, wherein bait set panel captures all or substantially all of the cfDNA, or amplification products thereof, from the hotspot regions in the sample and a portion of the cfDNA, or amplification products thereof, from the backbone regions in the sample.

3. The method of claim 1, wherein the targeted genomic regions of interest include single nucleotide variants and/or indels.

4. The method of claim 1, wherein the backbone and/or hotspot regions comprise regions from tumor-relevant marker genes.

5. The method of claim 4, wherein the tumor relevant marker genes include BRAF, BRCA, EGFR, KRAS, PIK3CA, ROS1, and/or TP53.

6. The method of claim 1, wherein a read budget is allocated to the sample.

7. The method of claim 6, wherein the read budget is between 100,000,000 reads and 100,000,000,000 reads.

8. The method of claim 6, wherein the read budget is between 500,000,000 reads and 50,000,000,000 reads.

9. The method of claim 6, wherein the read budget is between 1,000,000,000 reads and 5,000,000,000 reads across 20,000 bases to 100,000 bases.

10. The method of claim 1, wherein the method comprises detecting a genetic variant, wherein the sensitivity of detecting the genetic variant in the sample is higher for genetic variants in the hotspot regions compared to the sensitivity of detecting genetic variants in the backbone regions.

11. The method of claim 1, wherein baits in the bait set panel are target-specific oligonucleotides.

12. The method of claim 1, wherein: (i) the sample comprises a predetermined amount of cfDNA; (ii) the baits that target the hotspot regions are provided in an amount such that DNA from the hotspot regions is captured at saturation; and (iii) the baits that target the backbone regions are provided in an amount such that DNA from the backbone regions is captured below saturation.

13. The method of claim 1, wherein the sequence reads are analyzed for cancer-relevant genetic variants.

14. The method of claim 13, wherein redundant sequence reads from an original nucleic acid in the sample are collapsed into a consensus sequence representing the original nucleic acid.

15. The method of claim 1, wherein the cfDNA is isolated from blood or serum.

16. The method of claim 1, wherein the cfDNA comprises circulating tumor DNA.

17. The method of claim 1, wherein the bait set panel comprises baits that selectively enrich for one or more nucleosome-associated regions of a genome, the nucleosome-associated regions comprising genomic regions having one or more genomic base positions with differential nucleosomal occupancy, wherein the differential nucleosomal occupancy is characteristic of a cell or tissue type of origin or disease state.

18. A method for multi-resolution analysis of cell-free DNA (cfDNA) comprising:
(a) providing a sample comprising cfDNA;
(b) enriching cfDNA, or amplification products thereof, from hotspot regions and backbone regions, using a bait set panel which preferentially enriches for the hotspot regions compared to the backbone regions to provide an enriched set of nucleic acids, wherein the backbone regions are larger genomic regions compared to the genomic regions of the hotspot regions;
(c) sequencing the enriched set of nucleic acids, or amplification products thereof, wherein the enrichment results in higher average read depth for the hotspot regions compared to the average read depth for the backbone regions; and
(d) detecting a genetic variant, wherein the sensitivity of detecting the genetic variant in the sample is higher for genetic variants in the hotspot regions compared to the sensitivity of detecting genetic variants in the backbone regions.

19. A method for multi-resolution analysis of cell-free DNA (cfDNA) comprising:
(a) providing a sample comprising cfDNA;
(b) enriching cfDNA, or amplification products thereof, from hotspot regions and backbone regions, using a bait set panel which preferentially enriches for the hotspot regions compared to the backbone regions to provide an enriched set of nucleic acids, wherein the backbone regions are larger genomic regions compared to the genomic regions of the hotspot regions; and
(c) sequencing the enriched set of nucleic acids, or amplification products thereof, wherein the enrichment results in higher average read depth for the hotspot regions compared to the average read depth for the backbone regions,
wherein: (i) the sample comprises a predetermined amount of cfDNA; (ii) the baits that target the hotspot regions are provided in an amount such that DNA from the hotspot regions is captured at saturation; and (iii) the baits that target the backbone regions are provided in an amount such that DNA from the backbone regions is captured below saturation.

* * * * *